(12) United States Patent
Giambattista

(10) Patent No.: US 10,881,795 B2
(45) Date of Patent: Jan. 5, 2021

(54) AUTO-INJECTOR DEVICE

(71) Applicant: L.G.P. TECHNOLOGY HOLDINGS LLC, East Hanover, NJ (US)

(72) Inventor: Lucio Giambattista, East Hanover, NJ (US)

(73) Assignee: L.G.P. TECHNOLOGY HOLDINGS LLC, Cheyenne, WY (US)

(*) Notice: Subject to any disclaimer, the term of this patent is extended or adjusted under 35 U.S.C. 154(b) by 0 days.

(21) Appl. No.: 16/479,510

(22) PCT Filed: Jan. 20, 2018

(86) PCT No.: PCT/US2018/014591
§ 371 (c)(1),
(2) Date: Jul. 19, 2019

(87) PCT Pub. No.: WO2018/136840
PCT Pub. Date: Jul. 26, 2018

(65) Prior Publication Data
US 2019/0328968 A1    Oct. 31, 2019

Related U.S. Application Data

(60) Provisional application No. 62/448,834, filed on Jan. 20, 2017, provisional application No. 62/461,477, filed on Feb. 21, 2017.

(51) Int. Cl.
*A61M 5/20* (2006.01)
*A61M 5/24* (2006.01)
(Continued)

(52) U.S. Cl.
CPC ............ *A61M 5/20* (2013.01); *A61M 5/2455* (2013.01); *A61M 5/315* (2013.01); *A61M 5/3221* (2013.01)

(58) Field of Classification Search
CPC ...... A61M 5/2033; A61M 5/20; A61M 5/178; A61M 5/3205; A61M 5/32; A61M 5/31;
(Continued)

(56) References Cited

U.S. PATENT DOCUMENTS 2,752,918 A * 7/1956 Uytenbogaar ...... A61M 5/2033
604/136
2,866,458 A * 12/1958 Hein, Jr. ............. A61M 5/2033
604/138
(Continued)

FOREIGN PATENT DOCUMENTS

CN    102137691 A    7/2011
WO    2009010591 A2    1/2009
(Continued)

*Primary Examiner* — Nathan R Price
*Assistant Examiner* — Mark A Igel
(74) *Attorney, Agent, or Firm* — Weitzman Law Offices, LLC

(57) ABSTRACT

An auto-injector for hypodermic delivery of medication includes a first subassembly releasably coupled to a second subassembly. The first subassembly includes a cartridge holder configured to receive a medication cartridge, an injection needle through which medication can pass from the medication cartridge, and a needle shield movable between an extended position enclosing the needle and a retracted position in which a proximal end of the needle is not enclosed by the needle shield. The second subassembly includes a movable plunger rod positioned within a housing. Movement of the needle shield in a proximal direction from the retracted position to the extended position following administration of the medication automatically releases the first subassembly from the second subassembly. The released first subassembly is locked with the needle shield in the extended position. A new first subassembly containing
(Continued)

an unused dosage of medication may be inserted and releasably connected to the second subassembly.

50 Claims, 20 Drawing Sheets

(51) Int. Cl.
*A61M 5/315* (2006.01)
*A61M 5/32* (2006.01)

(58) Field of Classification Search
CPC .. A61M 5/321; A61M 5/3243; A61M 5/3271; A61M 5/24; A61M 5/2466; A61M 5/3202; A61M 5/002; A61M 5/3204; A61M 5/315; A61M 5/31533; A61M 5/31535; A61M 5/3245; A61M 5/31501; A61M 5/3213; A61M 5/3158; A61M 5/31585; A61M 5/31583; A61M 5/31576; A61M 5/31565; A61M 5/2455; A61M 5/3221; A61M 2005/2474; A61M 2005/2524

See application file for complete search history.

(56) References Cited

U.S. PATENT DOCUMENTS

| | | | | |
|---|---|---|---|---|
| 3,797,489 A | * | 3/1974 | Sarnoff | A61M 5/2033 604/136 |
| 3,880,163 A | * | 4/1975 | Ritterskamp | A61M 5/2033 604/136 |
| 5,378,233 A | * | 1/1995 | Haber | A61M 5/19 604/135 |
| 5,658,259 A | * | 8/1997 | Pearson | A61M 5/2033 604/136 |
| 6,656,163 B1 | * | 12/2003 | Marshall | A61M 5/2033 222/325 |
| 7,794,432 B2 | * | 9/2010 | Young | A61M 5/31596 604/192 |
| 9,242,053 B2 | * | 1/2016 | Wozencroft | A61M 5/5013 |
| 2003/0014018 A1 | * | 1/2003 | Giambattista | A61M 5/002 604/198 |
| 2003/0144633 A1 | * | 7/2003 | Kirchhofer | A61M 5/2033 604/201 |
| 2005/0033230 A1 | * | 2/2005 | Alchas | A61M 5/326 604/117 |
| 2005/0101919 A1 | * | 5/2005 | Brunnberg | A61M 5/2033 604/197 |
| 2007/0073232 A1 | * | 3/2007 | Pickhard | A61M 5/2033 604/134 |
| 2010/0152659 A1 | | 7/2010 | Streit et al. | |
| 2010/0249705 A1 | | 9/2010 | Kronestedt | |
| 2010/0249721 A1 | * | 9/2010 | Guillermo | A61M 5/2033 604/246 |
| 2011/0034879 A1 | * | 2/2011 | Crow | A61M 5/2033 604/197 |
| 2011/0251553 A1 | * | 10/2011 | Ratjen | A61M 5/2033 604/89 |
| 2012/0041389 A1 | * | 2/2012 | Giambattista | A61M 5/2033 604/228 |
| 2012/0123350 A1 | * | 5/2012 | Giambattista | A61M 5/2033 604/198 |
| 2014/0207106 A1 | * | 7/2014 | Bechmann | A61M 5/3204 604/506 |
| 2015/0045729 A1 | * | 2/2015 | Denzer | A61M 5/20 604/110 |
| 2015/0174325 A1 | * | 6/2015 | Young | A61M 5/2033 604/135 |
| 2015/0297833 A1 | * | 10/2015 | Henderson | A61M 5/2033 604/135 |
| 2015/0335829 A1 | * | 11/2015 | Giambattista | A61M 5/3146 604/192 |
| 2016/0106920 A1 | * | 4/2016 | Stefansen | A61M 5/2033 604/198 |
| 2016/0213858 A1 | * | 7/2016 | Hogdahl | A61M 5/2033 |
| 2016/0271319 A1 | * | 9/2016 | Bengtsson | A61M 5/2466 |
| 2016/0287810 A1 | * | 10/2016 | Keim | A61M 5/3204 |
| 2016/0361503 A1 | * | 12/2016 | Bendek | A61M 5/20 |

FOREIGN PATENT DOCUMENTS

| WO | 2012003516 A2 | 1/2012 |
|---|---|---|
| WO | 2015197866 A1 | 12/2015 |

* cited by examiner

AUTO-INJECTOR DEVICE

CROSS-REFERENCE TO RELATED APPLICATIONS

This application is a continuation of and claims priority to U.S. Provisional Patent Application Nos. 62/448,834 (filed Jan. 20, 2017) and 62/461,477 (filed Feb. 21, 2017), the entirety of each of which is incorporated herein by reference.

TECHNICAL FIELD

This disclosure relates generally to drug delivery devices, and more specifically, to an auto-injector for administering injectable medication.

BACKGROUND

One of the fastest emerging drug delivery devices today is the auto-injector, which is commonly used to administer a single dose of a particular medication. Typically, auto-injectors are intended for self-administration of a predetermined dosage of medication by the patient or an untrained user. This is particularly important in potentially life-threatening medical emergencies, such as, for example, a patient or user suffering from an anaphylaxis condition caused by a severe allergic reaction. Patients who may be prone to sudden anaphylaxis are often prescribed an auto-injector having a predetermined dose of epinephrine (such as an EpiPen®) or other medication for immediate injection into a patient or user in the event of sudden anaphylaxis. As such, auto-injectors must be safe, reliable and easy to use.

Many auto-injectors today include a cartridge that is pre-filled with a particular medication. Such devices are commonly spring- or mechanically-loaded to automatically administer a predetermined dosage of the pre-filled medication through a needle when activated by the auto-injector needle shield being pressed against the patient's or user's skin during needle insertion. In other auto-injectors, a button may be included on the auto-injector device to automatically activate injection through the push of the button.

There is, however, an urgent need to minimize the cost of auto-injectors, while, at the same time, ensuring that the devices are safe, reliable and easy to use for self-administration. While some manufacturers have attempted to reduce costs through use of reusable auto-injector devices, such reusable devices are not always optimal over a disposable auto-injector device. This is because some patients may not be able to reload a replacement cartridge into the reusable auto-injector device and, if not done properly, the sterility of the medication may be compromised and/or the reloaded device may not operate as designed.

SUMMARY

In one aspect of this disclosure, an auto-injector for hypodermic delivery of medication includes a first subassembly releasably coupled to a second subassembly. The first subassembly includes a cartridge holder configured to receive a medication cartridge, a hollow injection needle having a longitudinal cavity through which medication can pass from the medication cartridge, and a needle shield moveable relative to the cartridge holder between an extended position enclosing the needle and a retracted position in which at least a proximal end of the needle is not enclosed by the needle shield. The second subassembly includes a housing, and a moveable plunger rod positioned within the housing. Movement of the needle shield in a proximal direction from the retracted position to the extended position following administration of the mediation will automatically release the first subassembly from the second subassembly.

The released first subassembly is locked with the needle shield in the extended position. A new first subassembly containing an unused dosage of medication may be inserted and releasably connected to the second subassembly.

In another aspect of this disclosure, an auto-injector for hypodermic delivery of medication includes a housing and a medication cartridge positioned within the housing, the cartridge including a pierceable septum. An injection needle having a longitudinal cavity therethrough is also positioned within the housing, the needle being moveable between a first position and a second position, wherein, in the first position, the needle cavity is not in fluid communication with an interior of the cartridge, and in the second position, the needle cavity is in fluid communication with the interior of the cartridge. A removable cap is releasably attached to the housing, such that during removal of the cap from the housing, the needle moves from the first position to the second position so as to cause a distal end of the needle to pierce the septum of the cartridge.

In yet another aspect of this disclosure, an auto-injector for hypodermic delivery of medication includes a housing and a cartridge holder positioned within the housing and configured to receive a medication cartridge, the cartridge holder being moveable between a first position and a second position proximal from the first position, wherein, in the first position, the cartridge holder is prevented from moving in a proximal direction. A moveable plunger rod is also positioned within the housing and biased to move in the proximal direction. A plunger release latch positioned within the housing releasably retains the plunger rod in a locked position. A hollow injection needle having a longitudinal cavity through which medication can pass from the medication cartridge. A needle shield is movable relative to the cartridge holder between an extended position enclosing the needle and a retracted position in which at least an end of the needle is not enclosed by the needle shield. Distal movement of the needle shield both releases the cartridge holder from the first position and releases the latch to allow the plunger rod to move in the proximal direction and urge the cartridge holder from the first position to the second position.

In yet another aspect of this disclosure, a subassembly for an auto-injector includes a cartridge holder configured to receive a medication cartridge, and a hollow injection needle having a longitudinal cavity therethrough through which medication can pass from the medication cartridge. A needle shield is movable relative to the cartridge holder between an extended position enclosing the needle and a retracted position in which at least an end of the needle is not enclosed by the needle shield. A shell at least partially encompasses the cartridge holder and the needle shield. A removable cap releasably locks the shell and needle shield such that, when in place, the cap prevents the needle shield and shell from moving relative to each other and, when removed, allows relative movement between the shell and needle shield. The shell is configured to releasably connect to a second subassembly so as to form the auto-injector.

DETAILED DESCRIPTION

With reference to the accompanying drawings, various embodiments of the invention are described more fully below. Some, but not all, embodiments are shown. Various embodiments may be embodied in many different forms and should not be construed as limited to the embodiments expressly described. Like numbers refer to like elements throughout. The singular forms "a," "an" and "the" include the singular and plural unless the context clearly dictates otherwise.

Figure 1:
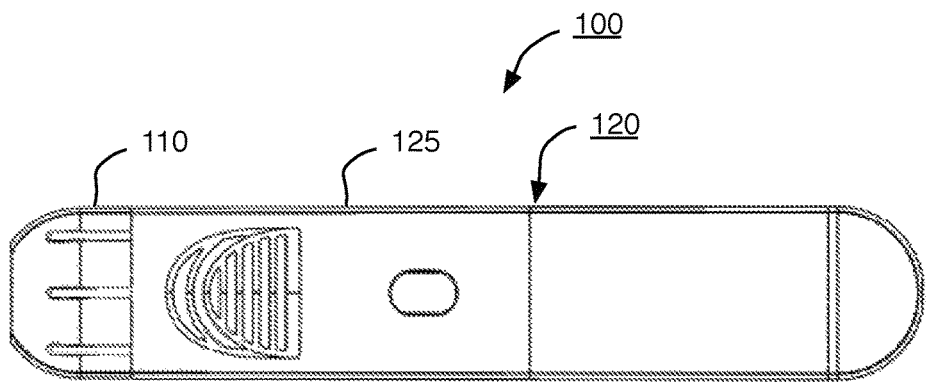
FIG. 1 is plan view of an auto-injector device according to one aspect of this disclosure.
Figure 2:
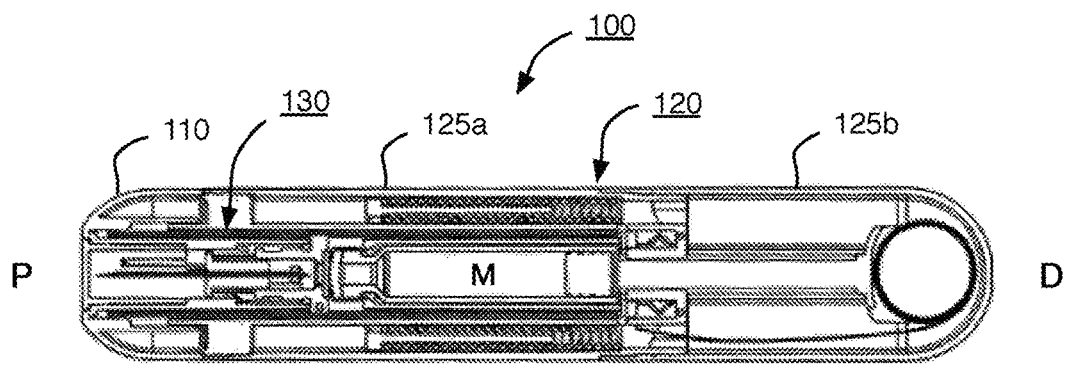
FIG. 2 is a cross-section of the auto-injector device of FIG. 1.

FIGS. 1 and 2 illustrate an exemplary embodiment of a semi-disposable or fully disposable auto-injector device 100 capable of safely, reliably and easily delivering a predetermined dosage of medication M to a patient. The auto-injector device 100 includes a removable needle cap 110 located on a proximal end P of the auto-injector device, a rear subassembly 120 (which is reusable in a semi-disposable embodiment), and a front subassembly 130 (shown in FIG. 2) (which is disposable in a semi-disposable embodiment). The rear subassembly 120 includes a hollow housing 125, which can be a unitary component or multiple subcomponents. In the embodiment illustrated in FIGS. 1 and 2, the housing 125 includes a front body portion 125a coupled to a rear body cap 125b. The removable needle cap 110, rear subassembly 120, front subassembly 130, front body portion 125a, and rear body cap 125b are preferably formed from synthetic materials such as recyclable resins or any other suitable material that can be readily molded.

As used herein, the terms "proximal" and "distal" are used in reference to the position of the auto-injector device 100 relative the user of the device during injection. Thus, the proximal end P of the auto-injector device 100 refers to the end of the device that is closest to the user's skin during injection. Similarly, the distal end D of the auto-injector device 100 refers to the end of the device that is furthest from the injection location during use. In addition, a point located proximal to another point on the auto-injector device 100 would be closer to the proximal end P of the device, and a point located distal to another point on the device would be closer to the distal end D of the device.

Figure 3:
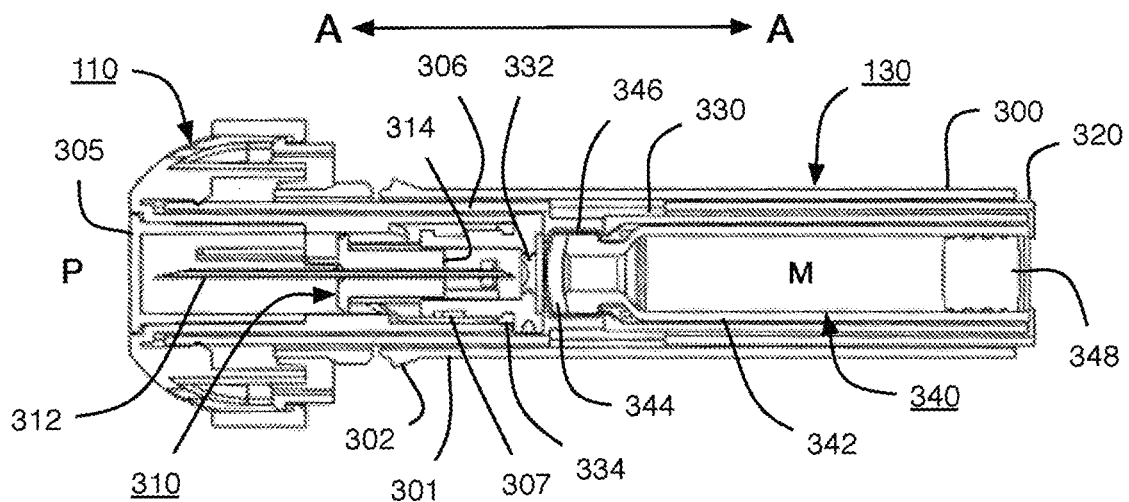
FIG. 3 is a cross-section of a front subassembly of the auto-injector device of FIG. 1.

FIG. 3 is a cross-section of one embodiment of the needle cap 110 and the front subassembly 130. The needle cap 110 is removably mounted on the proximal end P of the disposable body assembly 130 and may include a needle cap seal 305 for maintaining sterility of the needle assembly 310 prior to use. The needle cap seal 305 may be formed from an elastomeric material or any other suitable material to seal the proximal portion of the needle assembly 310 when the needle cap 110 is mounted on the front subassembly 130 prior to use.

The front subassembly 130 preferably includes front subassembly shell 300, needle assembly 310, needle shield 320, cartridge holder 330, seal 332 and ring seal 334. The seal 332 and ring seal 334 are preferably formed from an elastomeric material or any other suitable material for maintaining sterility of the needle assembly 310 prior to use. It is understood that seals 332, 334 may be separate components or formed as a unitary component that, for example, may be overmolded onto the cartridge holder 330 in a conventional manner. The needle assembly 310 includes a hollow injection needle 312 that extends through and is retained by a needle holder 314. The front subassembly shell 300, needle shield 320 and cartridge holder 330 are preferably formed from a synthetic material such as recyclable resins or any other suitable material that can be readily molded.

As will be discussed further below, when unlocked, the needle shield 320 is movable longitudinally (in the direction of Arrow A-A) within the front subassembly shell 300 between an extended position in which the shield 320 fully or substantially encloses the needle 312 and a retracted position in which the proximal end of the needle 312 may be exposed during injection.

The cartridge holder 330 is configured to hold a cartridge assembly 340 that is pre-filled with a predetermined dosage or volume of medication M. The cartridge assembly 340 includes a generally cylindrical, hollow cartridge body 342, which may be formed from glass or any other suitable material. The proximal end of the cartridge body 342 is preferably sealed with an elastomeric septum 344 and a cover 346, and the distal end of the cartridge body 342 is sealed with an elastomeric stopper or piston 348 that is movable longitudinally within the cartridge body 342 to expel a dosage of medicine M from the cartridge body when the auto-injector device 100 is actuated.

Figure 4:
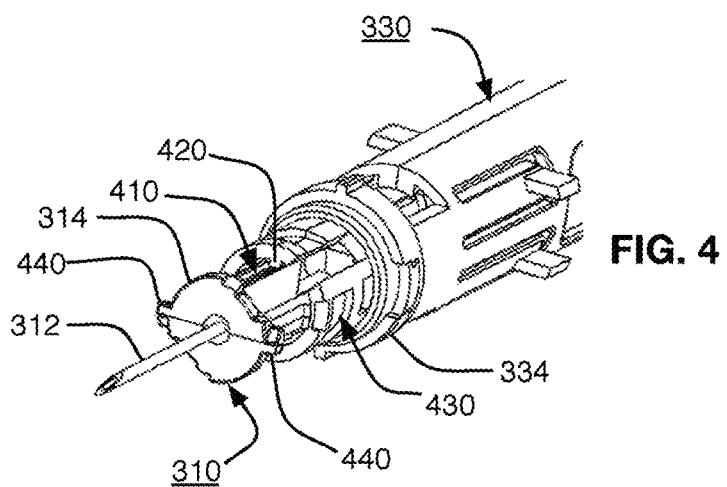
FIG. 4 is a perspective view of the needle assembly and proximal portion of the auto-injector device of FIG. 1.
Figure 4A:
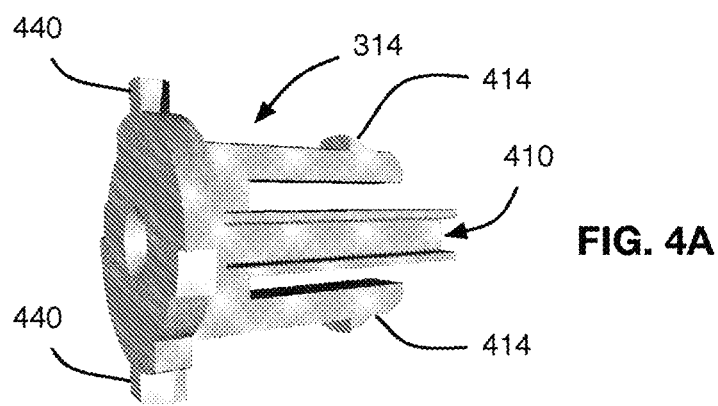
FIG. 4A is a side view of the needle holder of the needle assembly illustrated in FIG. 4.

Referring to FIGS. 4 and 4A, the needle holder 314 is slidably mounted within an opening on the proximal end of the cartridge holder 330. The needle holder 314 preferably includes at least one (and, more preferably, two) axial grooves 410 for receiving a corresponding spline 420 projecting inwardly from the proximal end of the cartridge holder 330 to prevent rotation of the needle holder assembly 310, while allowing the needle holder assembly to move longitudinally within the front subassembly 130 relative to the cartridge holder 330. In this manner, the needle holder 314 cannot rotate or otherwise move radially when the needle cap 110 is rotated during removal of the cap.

Figure 5:
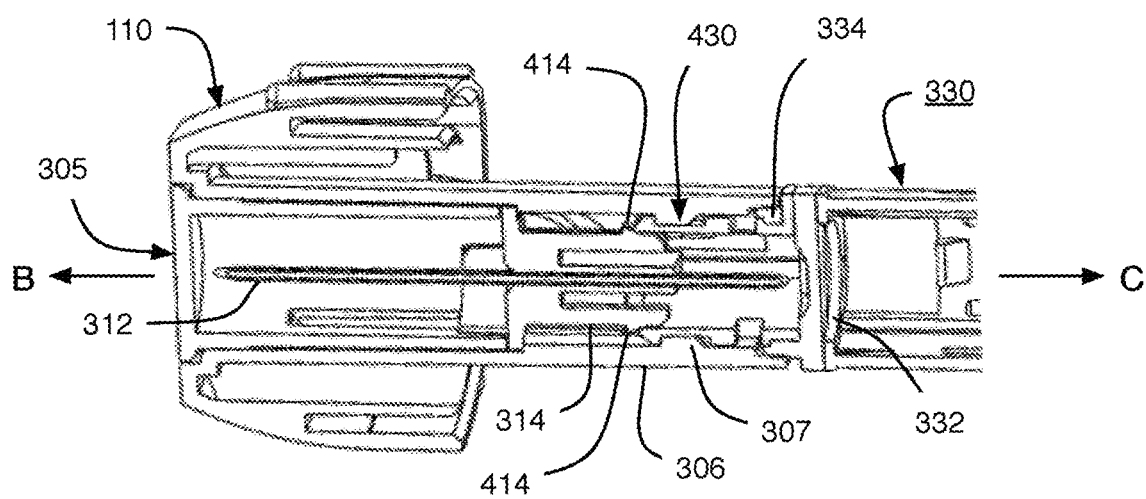
FIG. 5 is a cross-section of the needle cap assembled on the proximal portion of the front assembly of the auto-injector device of FIG. 1.

In one embodiment illustrated in FIGS. 4 and 5, a cam track or radially extending groove 430 is formed on the outer surface of and near the proximal end of the cartridge holder 330. As best seen in FIG. 5, The needle cap 110 preferably includes a hollow, generally cylindrical distal portion 306, which, when assembled on the front subassembly 130, extends over the cam track 430 on the proximal end of the cartridge holder 330. One or more cam followers 307 project inwardly from the generally cylindrical distal portion 306 of the needle cap 110 for corresponding engagement within the cam track 430 formed on the cartridge holder 330.

Figure 6:
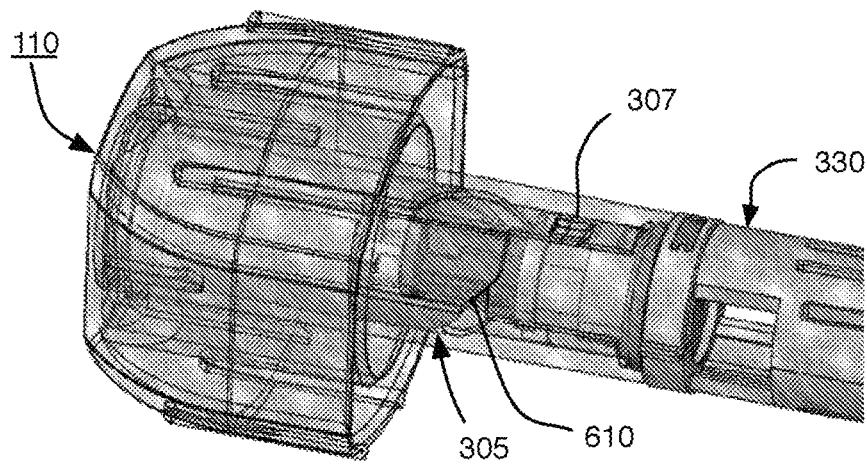
FIG. 6 is an enlarged cross section of the needle cap of FIG. 5 assembled on a proximal portion of the cartridge holder.
Figure 6A:
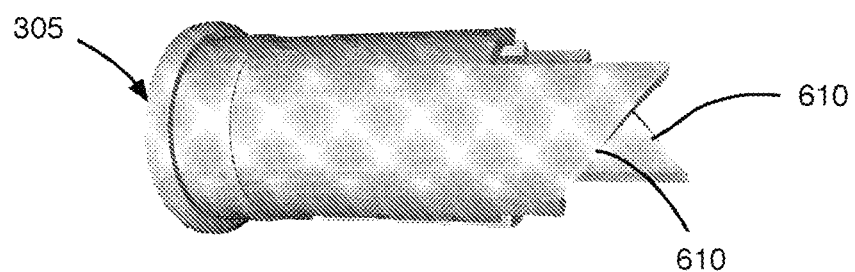
FIG. 6A is a side elevation view of the needle cap seal of the auto-injector device of FIG. 1.
Figure 6B:
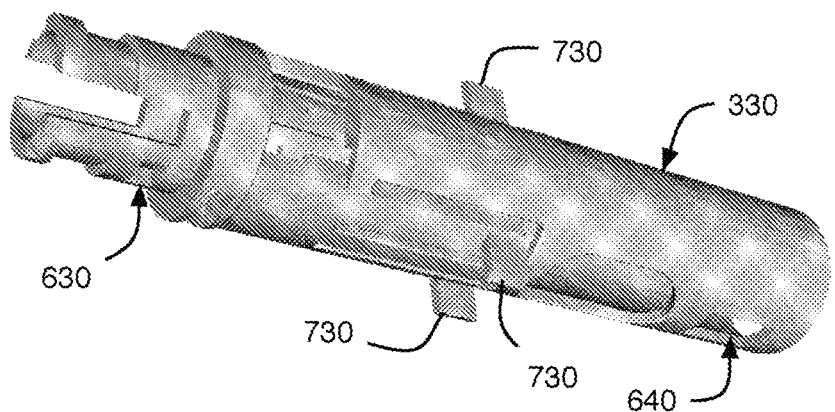
FIG. 6B is a side perspective view of the cartridge holder of the auto-injector device of FIG. 1.

In use, the one or more cam followers 307 are constrained within the cam track 430 on the cartridge holder 330 and prevent removal of the needle cap 110 until the cap is rotated to a position where the cam followers are in alignment with a corresponding relieved section 620 (FIG. 6B) of the cam track 430 that will enable the cap 110 to be pulled off the cartridge holder 330 (in the direction of Arrow B in FIG. 5) and removed from the auto-injector device 100.

As illustrated in FIGS. 3 and 5, when the needle cap 110 is installed on the unused auto-injector device 100, the needle assembly 310 is maintained sterile within the auto-injector device by the needle cap seal 305 on the removable cap 110, seal 332 on the cartridge holder 330, and ring seal 334 that is positioned about the proximal outer surface of the cartridge holder 330. In this embodiment, the distal portion 306 of the needle cap 110 preferably forms an interference fit around the ring seal 334 to form a seal.

As best seen in FIGS. 4, 4A, 5, 6, 6A and 6B, the distal portion of the needle cap seal 305 in this embodiment is configured as a cam ramp 610 that engages one or more corresponding cam followers 440 (FIGS. 4 and 4A) on a proximal end of the needle holder 314. When the user rotates the needle cap 110 relative to the cartridge holder 330 to initiate removal of the cap from the front subassembly 130, the cam ramp 610 engages one or more cam followers 440 on the needle holder 314, causing the needle assembly 310 to move longitudinally within the front subassembly 130 in the distal direction (Arrow C in FIG. 5) until the injection needle 312 pierces the seal 332 and septum 344 of the cartridge assembly 340. When in its final position, at least one (and preferably two) flexible hook-shaped member 414 extending from the distal portion of the needle holder 314 engage corresponding openings or recesses 630 in the cartridge holder 330 to lock the needle holder to the cartridge holder 330. The axial groove 410 formed in the needle holder 314 (FIG. 4A) constrains the corresponding spline 420 on the cartridge holder 330 to prevent the needle holder assembly 310 from rotating within the front subassembly 130 as the needle cap 110 is rotated.

Figure 7:
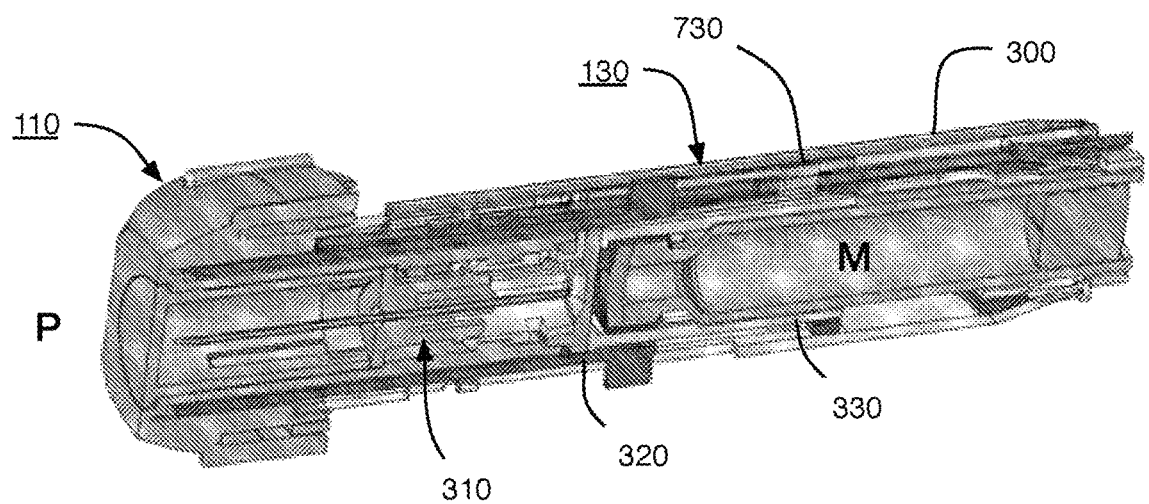
FIG. 7 is a cross-section of the needle cap assembled on the proximal portion of the front subassembly of the auto-injector device of FIG. 1.
Figure 8:
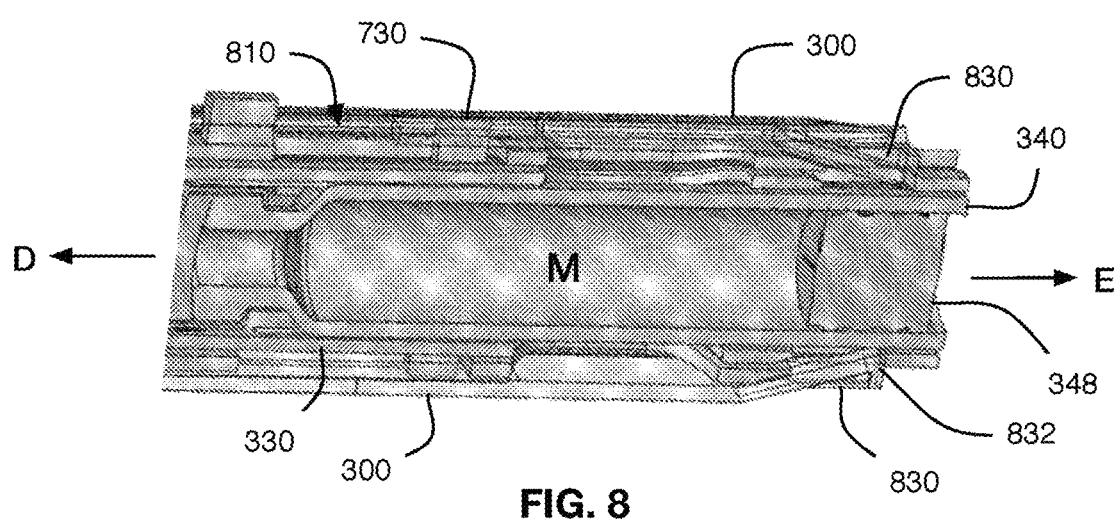
FIG. 8 is a cross section of a portion of the cartridge holder, needle shield and shell of the front subassembly of FIG. 7.
Figure 9:
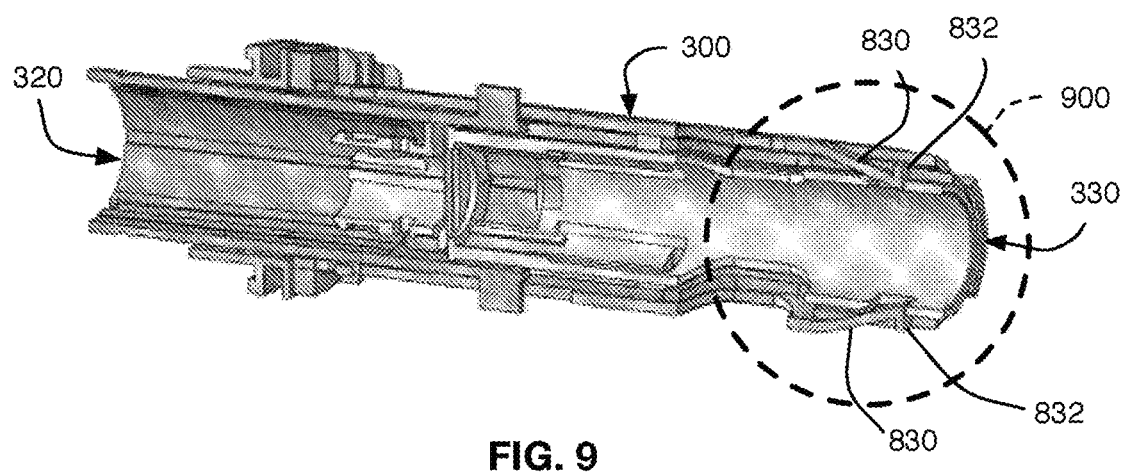
FIG. 9 is a cross section of the cartridge holder, needle shield and shell of the front subassembly of FIG. 7.
Figure 10:
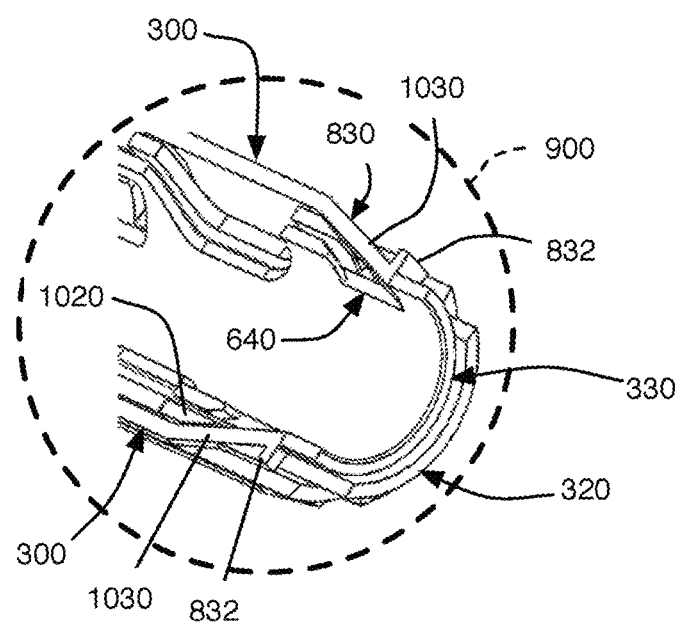
FIG. 10 is an enlarged cross section view of the distal portion of the cartridge holder, needle shield and shell of the front subassembly of FIG. 9.

Referring to FIGS. 6B and 7-10, the cartridge holder 330 is releasably locked to prevent movement longitudinally in the proximal direction (Arrow D of FIG. 8) by one or more (preferably two) flexible tabs 830 formed on the distal end of the front subassembly shell 300. As best seen in FIGS. 9 and 10, each flexible tab 830 on the front subassembly shell 300 preferably includes a ramp or bevel 1030 that terminates in a release latch or flange 832. In the releasably locked position, each flexible tab 830 preferably engages a corresponding opening 640 (best seen in FIGS. 6B and 10) formed in the cartridge holder 330 near its distal end such that the release latch 832 on the flexible tab 830 engages a portion of the cartridge holder defining the opening 640 to prevent longitudinal movement of the cartridge holder 330 in the proximal direction (Arrow D of FIG. 8) relative the front subassembly shell 300. The ramp 1030 on the flexible tab 830 engages a corresponding ramp or bevel 1020 on a distal portion of the needle shield 320 such that longitudinal movement of the needle shield 320 in the distal direction (Arrow E in FIG. 8) causes each ramp 1020 on the needle shield to engage a corresponding ramp 1030 on the flexible tab 830 to flex or otherwise move the flexible tab outward to disengage the latch 832 from the opening 640 in the distal portion of the cartridge holder 330. Once disengaged from the disposable housing 300, the cartridge holder 330 is released and free to move longitudinally in the proximal direction (Arrow D in FIG. 8) to perform needle penetration and drug delivery.

Figure 10A:
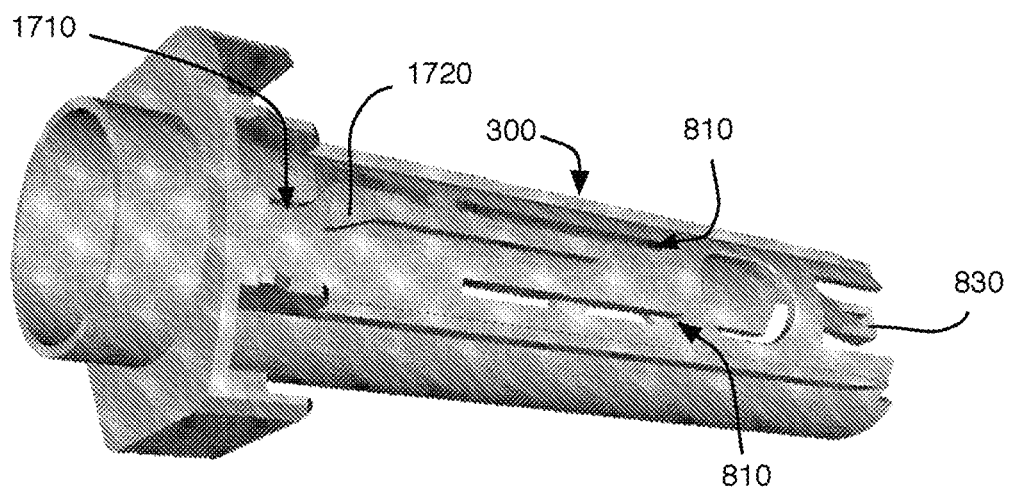
FIG. 10A is a side elevation view of the shell of the front subassembly of the auto-injector device of FIG. 1.
Figure 10B:
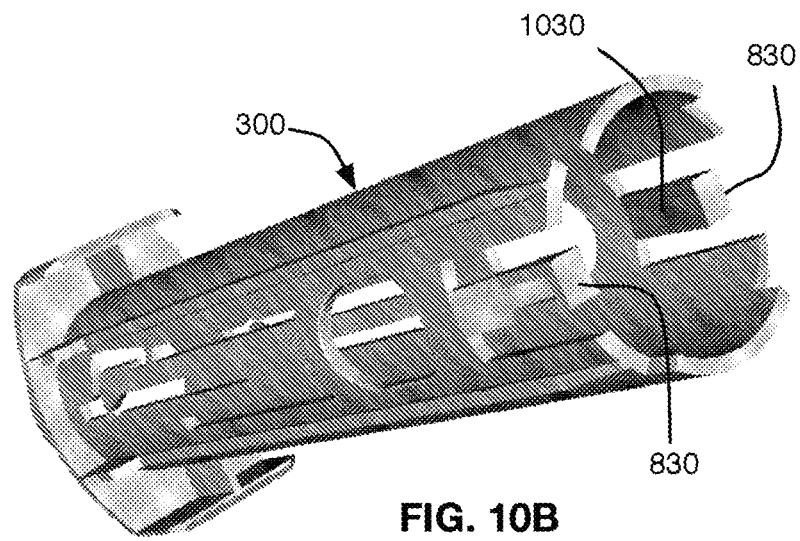
FIG. 10B is a perspective view of the distal end of the front subassembly shell of FIG. 10A.
Figure 10C:
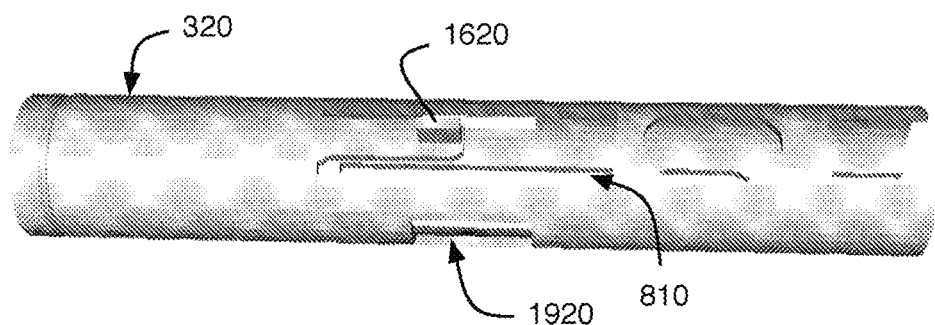
FIG. 10C is a side elevation view of the needle shield of the auto-injector device of FIG. 1.

Referring to FIGS. 7 and 8, the cartridge holder 330, needle shield 320, front subassembly shell 300 and needle cap 110 are all part of the interlock between each other in the front subassembly 130. The cartridge holder 330 preferably includes one or more outwardly projecting splines 730 (best seen in FIG. 6B) that extend through substantially coaligned axial grooves 810 formed in the needle shield 320 (FIG. 10C) and front subassembly shell 300 (FIG. 10A). In the releasably locked position as illustrated in FIG. 8, the spline 730 is constrained by the axial groove 810 and is bottomed out at the distal end of the axial groove 810 that is on the needle shield 320. This prevents the needle shield 320 from moving further longitudinally in the proximal direction (Arrow D) when the needle cap 110 is removed and the needle shield 320 is released and under the load of the needle shield spring ring 1152 or bracket 1150 (FIG. 11H). The cartridge holder 330 is held from moving longitudinally in both directions (Arrow D and Arrow E) because the needle cap 110 constrains it from moving longitudinally in the direction of Arrow E by pressing against the proximal end of the front subassembly shell 300 and it is prevented from moving longitudinally in the direction of Arrow D by the flex arms 830 on the front subassembly shell 300 that engage with corresponding openings 640 at the distal end of the cartridge holder 330.

Figure 11A:
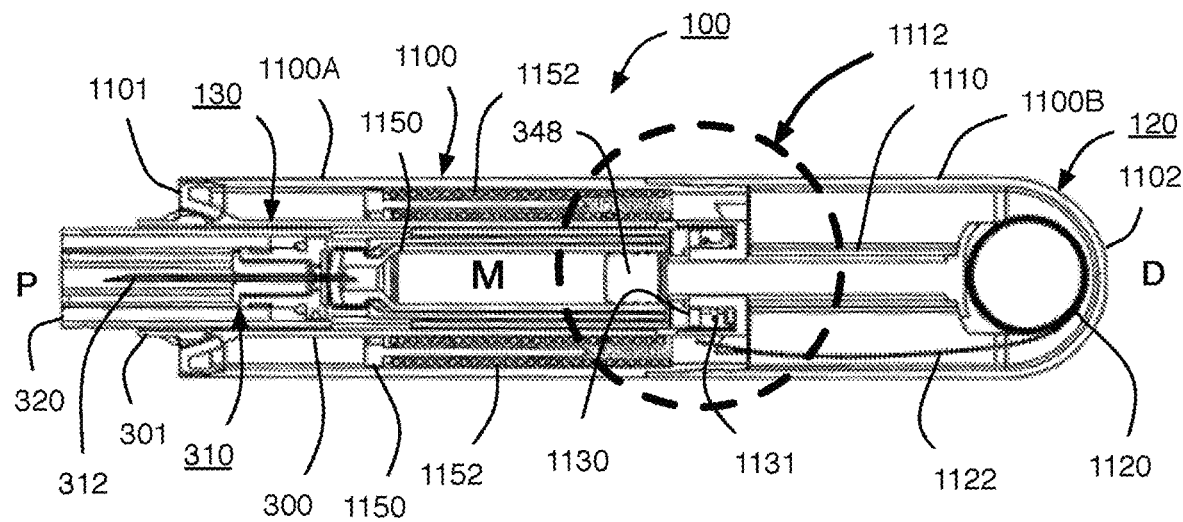
FIG. 11A is a cross-section of an assembled semi-disposable auto-injector device of without the needle cap.
Figure 11C:
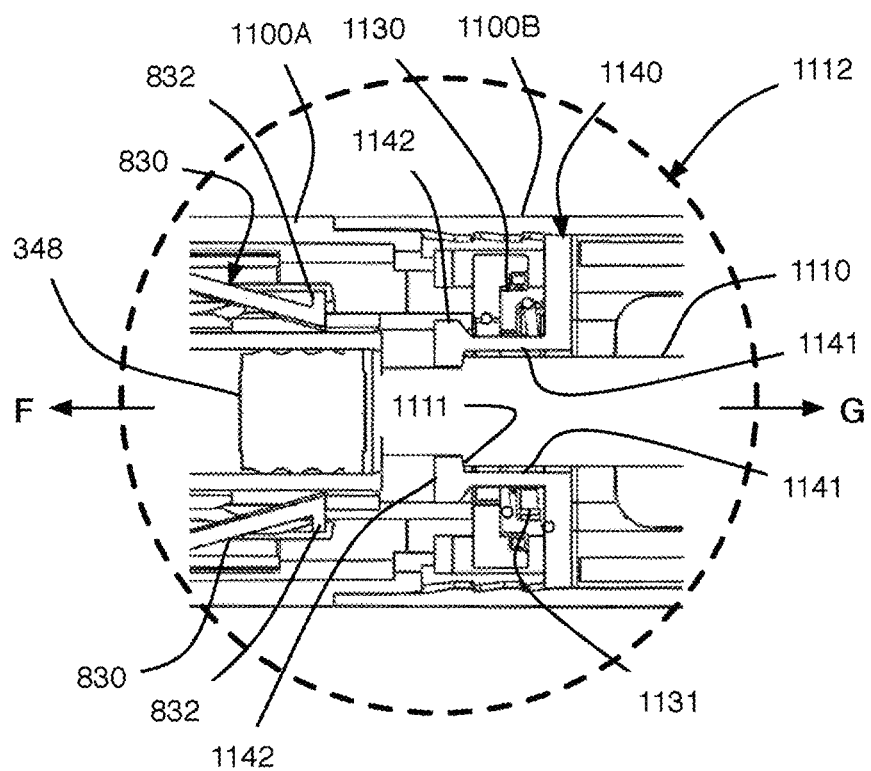
FIG. 11C is an enlarged cross-section of the release latch and trigger lock of FIG. 11A.

FIG. 11A illustrates a cross section of an assembled partially disposable auto-injector device 100 with the needle cap 110 removed. The reusable rear subassembly 120 includes a hollow, generally oval or elliptical shaped reusable housing 1100 having an opening at its proximal end 1101 for receiving the disposable housing assembly 130. The reusable housing 1100 is preferably closed at its distal end 1102 and can be formed as an integral construction or a combination of two or more components (reusable body front cap 1900, reusable body 1100A and reusable body rear cap 1100B in FIGS. 11C and 11E) that are configured to attach to one another to form the reusable housing 1100. The reusable housing 1100 is preferably made from synthetic materials such as recyclable resins or any other suitable material that can be readily molded.

Figure 11B:
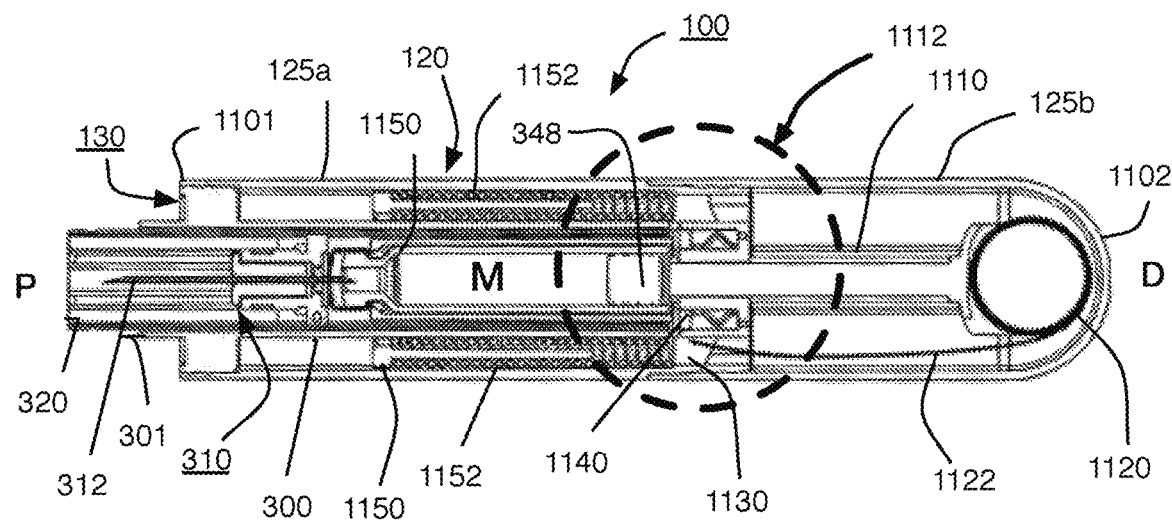
FIG. 11B is a cross-section of the assembled fully disposable auto-injector device without the needle cap.

FIG. 11B illustrates a cross section of an alternative assembled fully disposable auto-injector device 100 with the needle cap 110 removed. The housing 125 of the rear subassembly 120 preferably includes a hollow, generally oval or elliptical shaped front body portion 125a having an opening at its proximal end 1101 for receiving the front subassembly 130. The housing 125 is preferably closed at its distal end 1102 and can be formed as an integral construction or a combination of two or more components (front body 125a and rear body cap 125b in FIGS. 11D and 11F) that are configured to attach to one another to form the housing 125. The front body 125a and rear body cap 125b are preferably made from synthetic materials such as recyclable resins or any other suitable material that can be readily molded.

Within the housing of rear subassembly 120 is preferably a plunger 1110, plunger spring rotator 1120, plunger spring 1122, trigger lock 1130, needle shield spring ring 1150, and needle shield springs 1152.

Figure 11D:
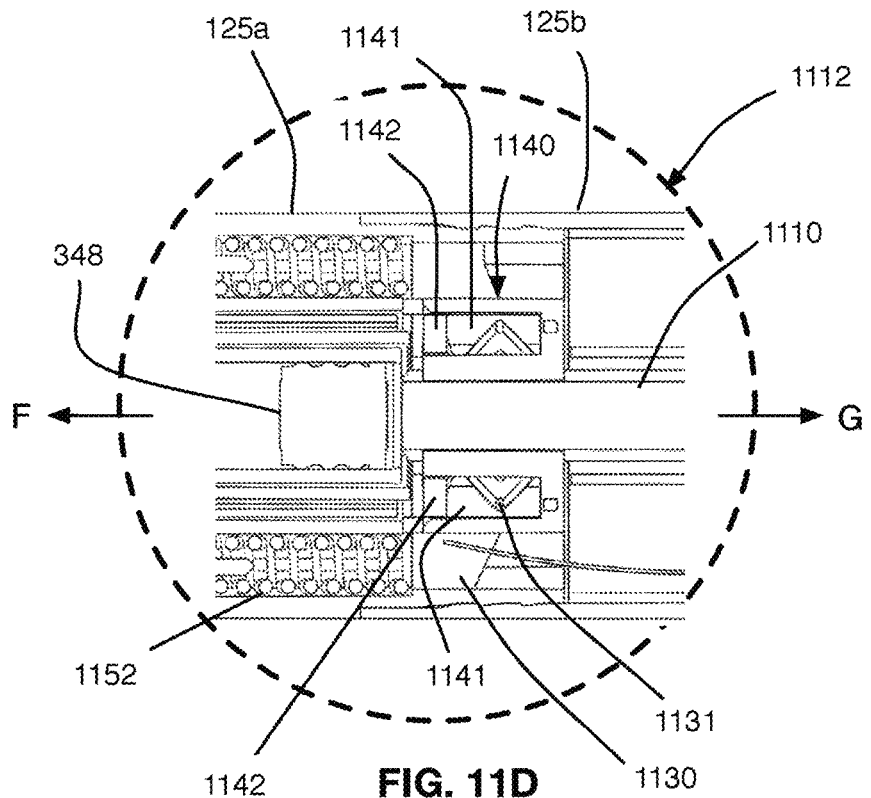
FIG. 11D is an enlarged cross-section of the release latch and trigger lock of FIG. 11B.
Figure 11E:
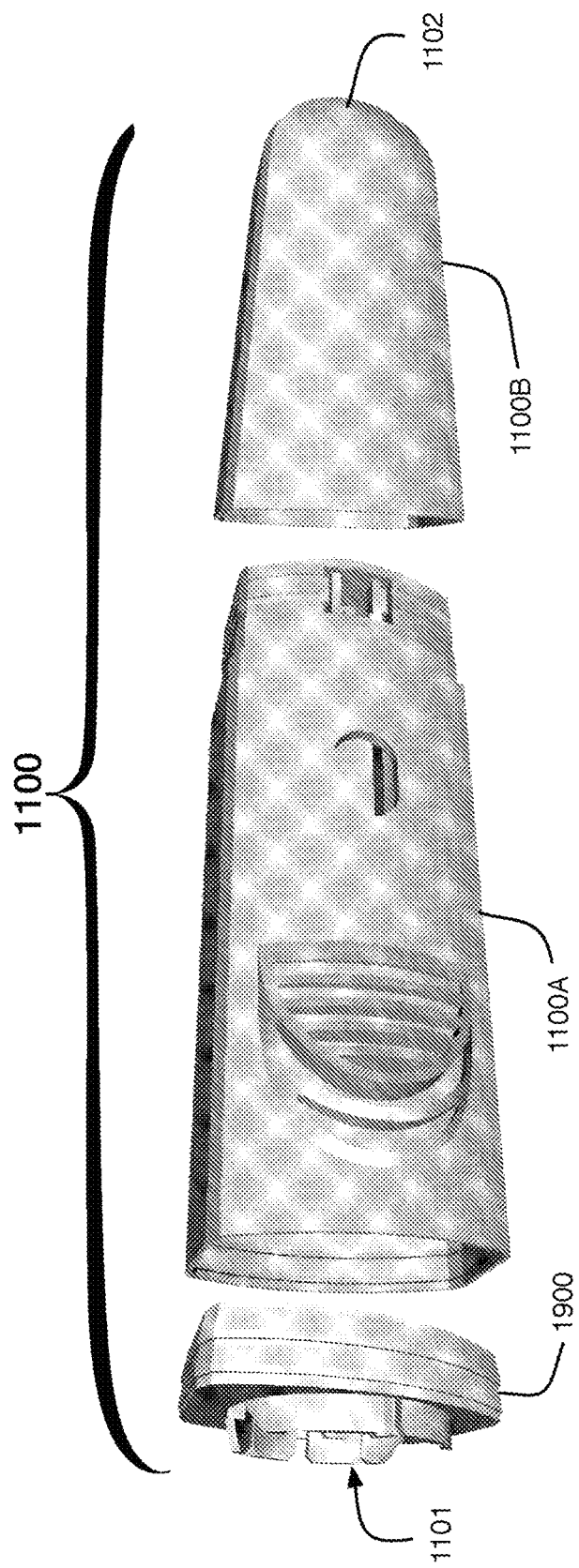
FIG. 11E is an exploded view of the reusable body of a semi-disposable auto-injector device.
Figure 11F:
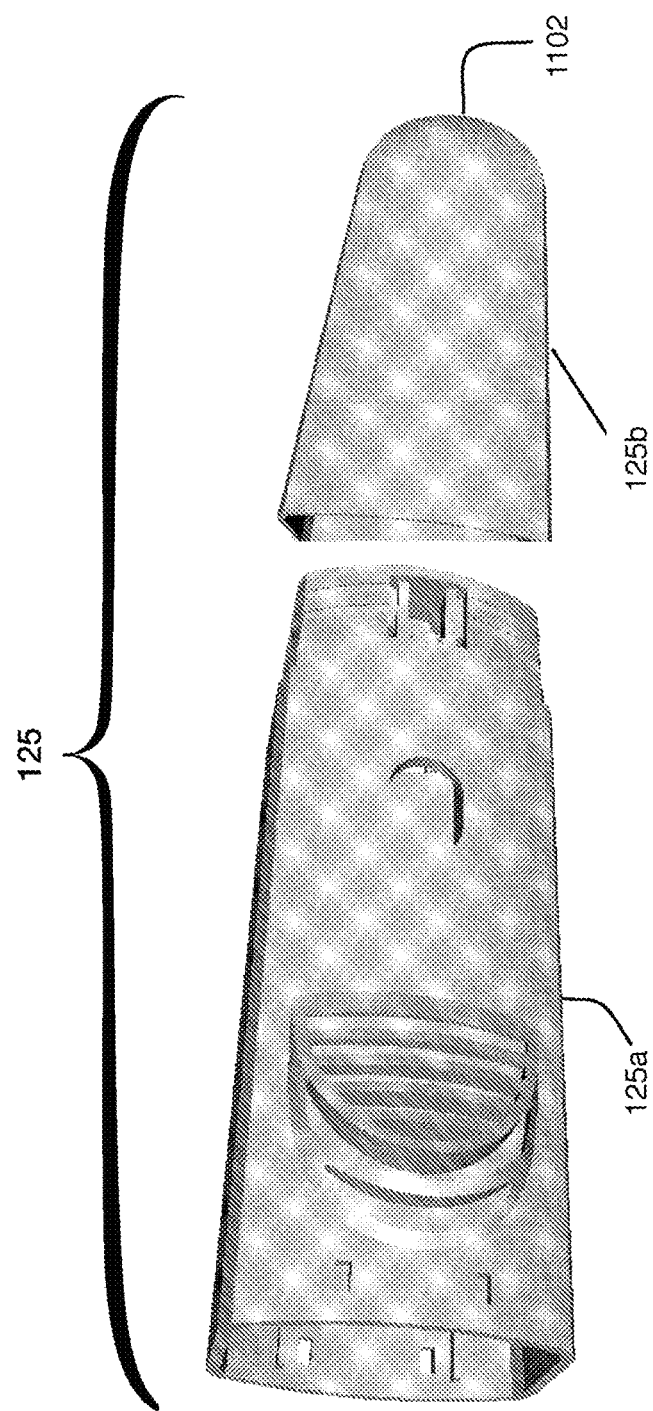
FIG. 11F is an exploded view of the front body and rear body cap of a fully disposable auto-injector device.

FIGS. 11C and 11D depict an enlarged view of the trigger lock 1130 and release latch 1140 illustrated in circle 1112 of FIGS. 11A and 11B respectively. The trigger lock 1130 and release latch 1140 releasably prevents the plunger 1110 from moving longitudinally in the proximal direction P (Arrow F of FIGS. 11C and 11D). In this embodiment, the release latch 140 is preferably integrally formed as part of the front body portion 125a of the housing 125. It is understood, however, that the release latch 1140 may be a separate component from the front body portion 125a.

Figure 11G:
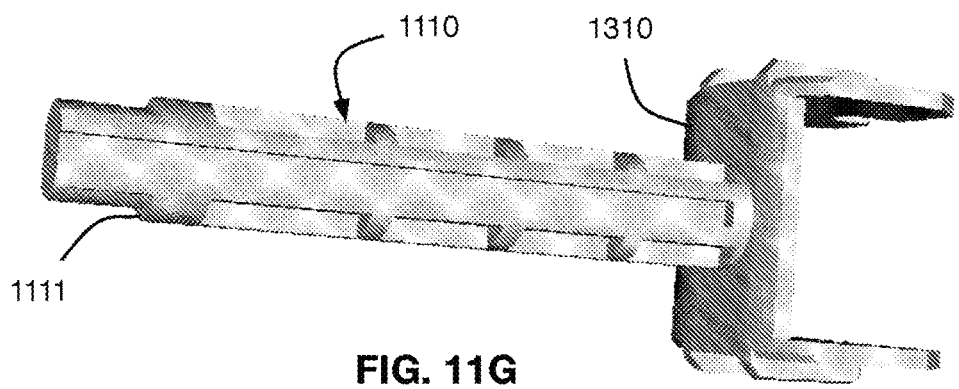
FIG. 11G is a side perspective view of the plunger of the auto-injector device of FIG. 1.
Figure 11H:
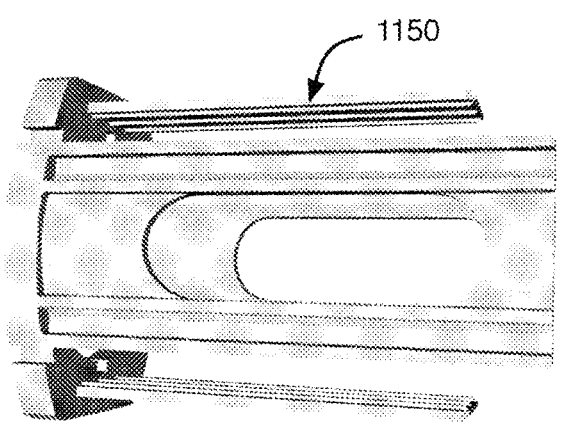
FIG. 11H is a side perspective view of the needle shield spring ring of the auto-injector device of FIG. 1.

The proximal end of the plunger 1110, which passes through an opening in the release latch 1140, preferably includes a shoulder 1111 (FIG. 11G). Referring to FIGS. 11C and 11D, the release latch 1140 includes one or more flexible arms 1141 terminating in an enlarged head 1142 that releasably engages the shoulder 1111 to prevent the plunger 1110 from moving longitudinally in the proximal direction P (Arrow F in FIGS. 11C and 11D) until the needle shield 320 is depressed fully or at least a minimum predetermined distance to activate the auto-injector device 100. The enlarged head 1142 on the flexible arm 1141 of the release latch 1140 is prevented from flexing outward by the trigger lock 1130.

Figure 11J:
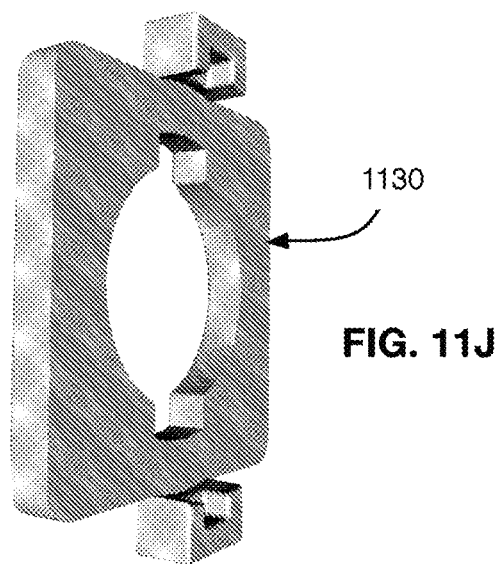
FIG. 11J is a side perspective view of the trigger lock of the auto-injector device of FIG. 1.

Referring to FIG. 11J, the trigger lock 1130 includes a base 1131 having an opening 1132 therethrough to accommodate the plunger 1110. A spring or biasing member 1133 extends from the base 1131. In this embodiment, the spring 1133 is formed as an integral part of the trigger lock 1130. It is understood, however, that the spring 1133 could alternative be a separate component from the trigger lock. The opening 1132 in the base 1131 includes one or more relieved sections 1132A to constrain the enlarged head on the flexible arm 1141 from flexing outward when the base 1130 is aligned with the enlarged head.

Figure 13:
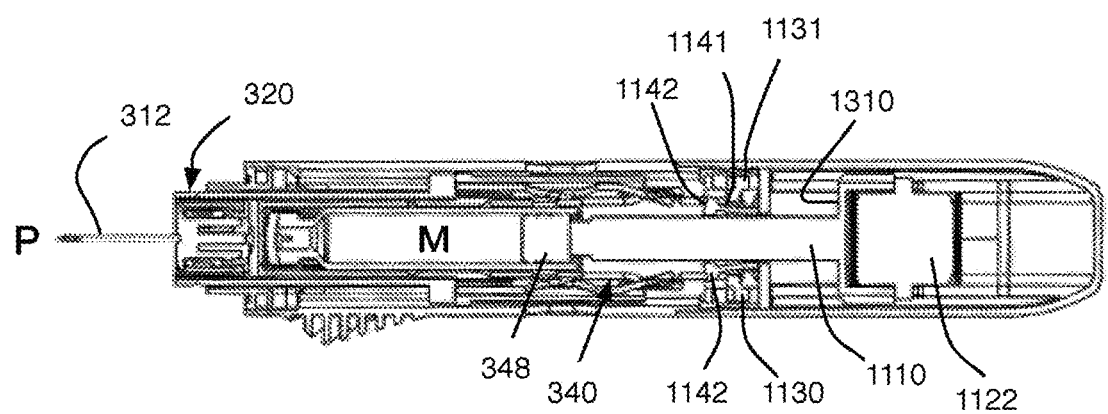
FIG. 13 is a cross-section of the auto-injector device of FIG. 11 during needle penetration.

Referring to FIG. 13, when the needle shield 320 is fully depressed, the base 1131 of the trigger lock 1130 (FIG. 11J) is moved longitudinally in the distal direction D (Arrow G in FIGS. 11C and 11D) against the biasing force of the spring portion 1133. When the relieved portion 1132A in the base 1131 no longer constrains the one or more flexible arms 1141 of the release latch 1140, the enlarged head 1142 on the one or more flexible arms 1141 flexes or bends radially outward to release the plunger 1110 and allow it to move longitudinally in the proximal direction P (Arrow F in FIGS. 11C and 11D) to begin needle penetration.

Figure 12A:
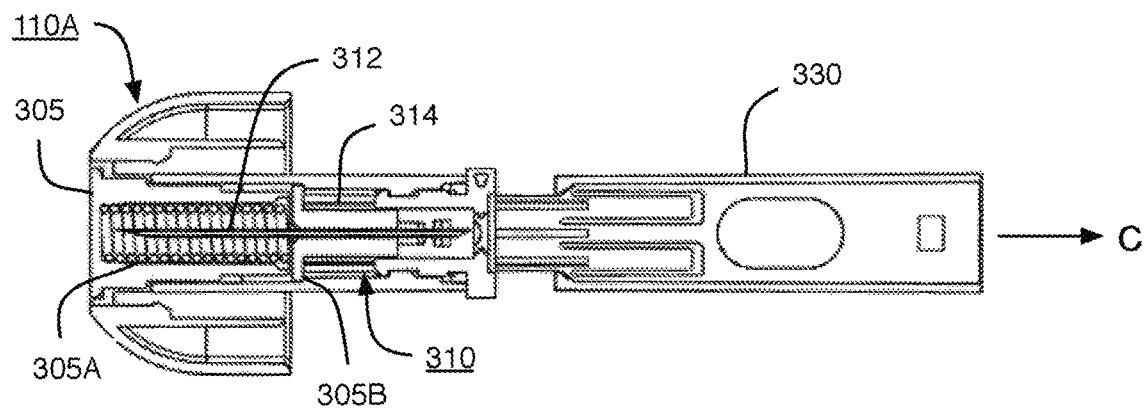
FIG. 12A is a cross section of an alternative embodiment of the needle cap with the needle assembly, needle holder and cartridge holder of the auto-injector device of FIG. 1.
Figure 12B:
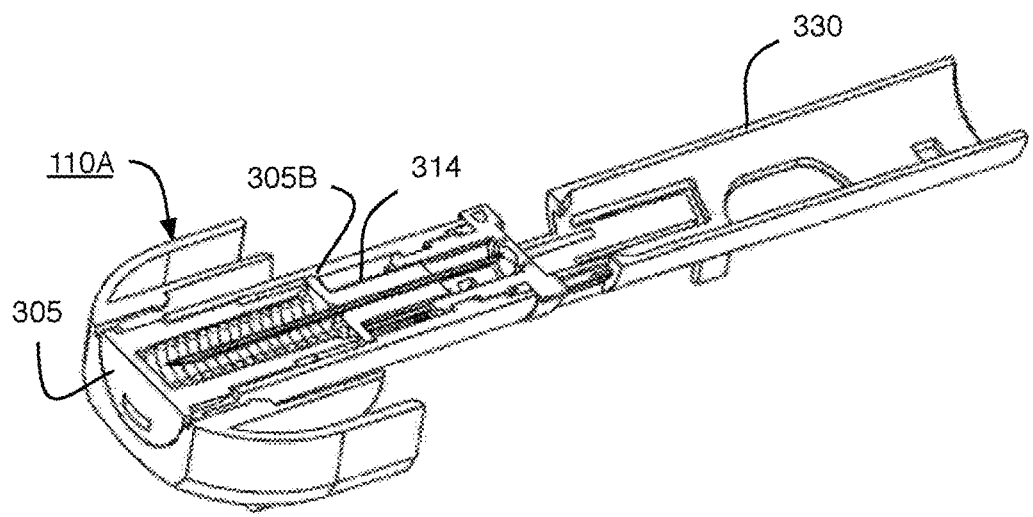
FIG. 12B is a perspective cross-sectional view of the alternative needle cap, needle assembly, needle holder and cartridge holder of FIG. 12A.

Alternative needle cap designs are also envisioned for use with the auto-injector device 100. For instance, in an alternative embodiment illustrated in FIGS. 12A-12F, a spring-loaded needle cap 110A is utilized to bias the needle assembly 310 longitudinally within the disposable body assembly 130 in the distal direction (Arrow C of FIG. 12A). The spring-loaded cap 110A is similar to needle cap 110 described above, except that, instead of the cam ramp 610 on the distal end of the needle cap seal 305, the cap 110A is spring loaded to automatically pierce the seal 332 and septum 344 of the cartridge assembly 340 when the cap 110A is turned. The sterility of the needle 312 is maintained in the same manner as described above with respect to needle cap 100.

The connection between the cap 110A and the cartridge holder 330 is the same as described above with respect to needle cap 100, except that the cap 110A can be turned in both directions (clockwise and counterclockwise). The needle holder 314 is biased in the direction of Arrow C (FIG. 12A) by the needle spring 305A, but is initially constrained from moving longitudinally in the distal direction (Arrow C) by two inwardly projecting flanges 305B formed on the interior of needle cap 110A.

Figure 12C:
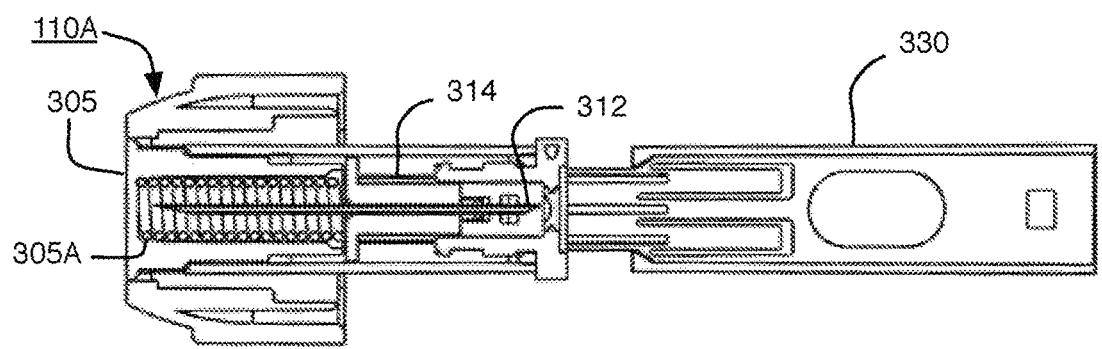
FIG. 12C is a cross section of the alternative needle cap of FIG. 12A with the needle assembly in its initial position.

Referring to FIG. 12C, once the needle cap 110A is rotated through a predefined angle (e.g., approximately 90°), the two flanges 305B no longer engage the needle holder 314. Since the needle holder 314 cannot rotate (it is radially engaged with the cartridge holder 330 as described above), there is nothing to prevent the needle holder from being biased longitudinally by the spring 305A in the distal direction (Arrow C of FIG. 12A).

Figure 12D:
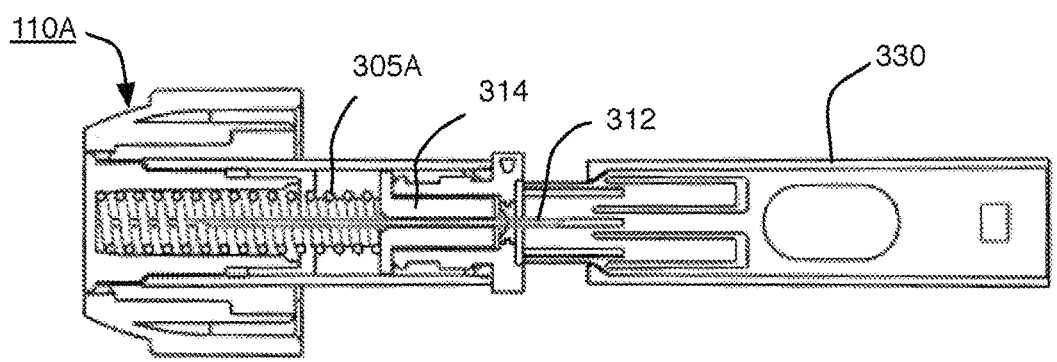
FIG. 12D is a is a cross section of the alternative needle cap of FIG. 12A with the needle assembly in its final position where the needle pierces the seal and septum of a cartridge assembly.

As illustrated in FIG. 12D, once the spring 305A pushes the needle holder 314 longitudinally in distal direction (Arrow C of FIG. 12A), the needle 312 pierces the seal 332 and the cartridge septum 344 (not shown). With further rotation of the needle cap 110A, counterforce from the spring 305A causes the needle cap to move longitudinally in the proximal direction (Arrow B of FIG. 5) to separate from the auto-injector device 100 and facilitate removal of the needle cap.

Figure 12E:
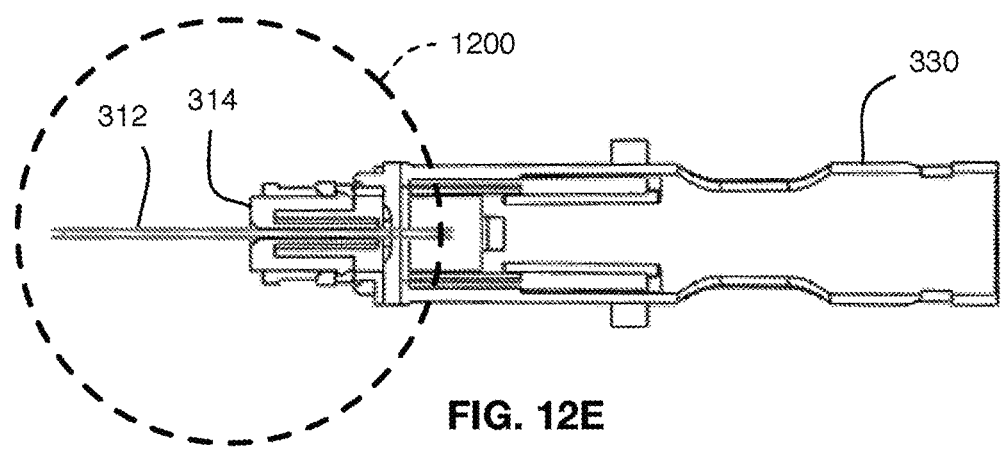
FIG. 12E is a cross section of the needle assembly locked in its final position on the cartridge holder.
Figure 12F:
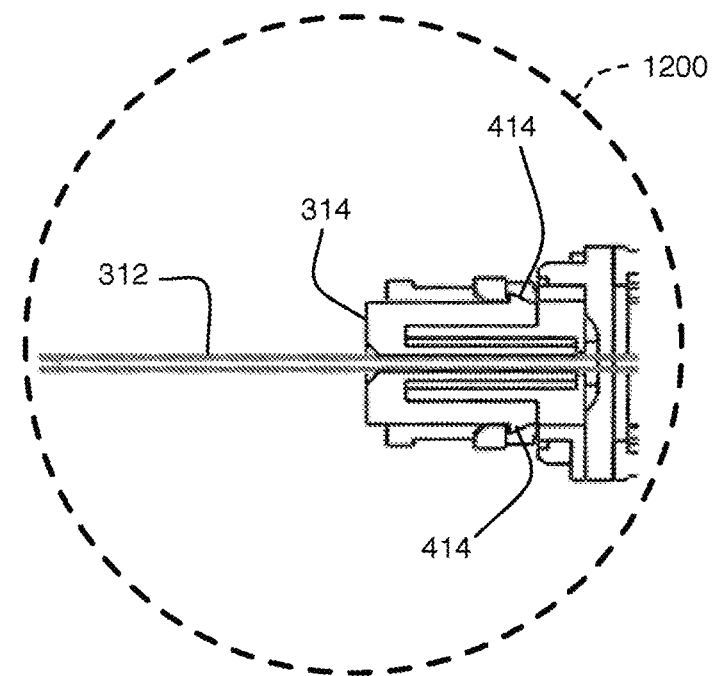
FIG. 12F is an exploded view of FIG. 12E with the needle assembly locked on the cartridge holder.

As illustrated in FIG. 12E and the enlarged view in FIG. 12F, when the needle holder 314 reaches its final position, each flexible hook-shaped member 414 extending from the distal portion of the needle holder 314 engages a corresponding opening 630 on the cartridge holder 330 to lock the needle holder in position on the cartridge holder.

Figure 12G:
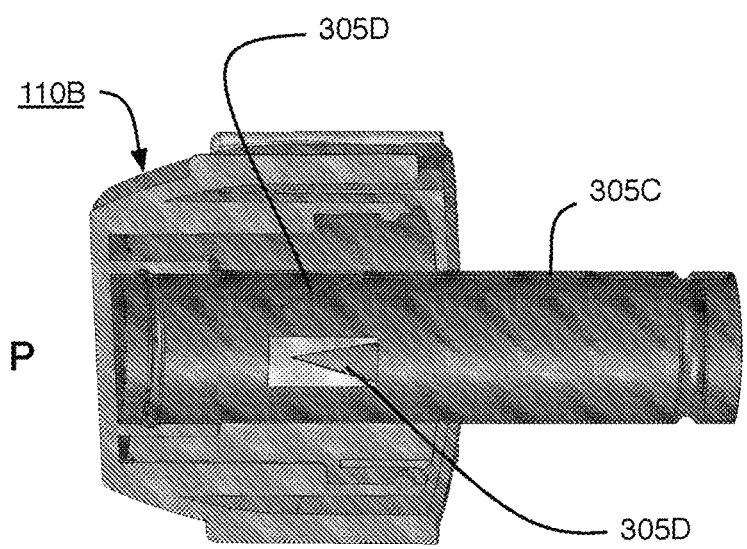
FIG. 12G is a cross section of a third embodiment of the needle cap.

In another alternative embodiment illustrated in FIG. 12G, a removable needle cap 110B may include a needle cap seal 305C having one or more inwardly projecting barbs 305D. The one or more barbs 305D are preferably angled in a direction toward the proximal end P of the auto-injector device 100 and are preferably made of metal or any other desired material having sufficient rigidity. An elastomeric needle tip cover (not shown) is releasably attached to a proximal end of the needle holder 314 to enclose and seal the portion of the injection needle 312 extending proximally from the needle holder 314. When assembled on the auto-injector device 100, the needle cap seal 305C within the removable needle cap 110B encloses at least a portion of the needle tip cover. In this alternative embodiment, the needle cap 110B may be removed from the auto-injector device 100 by pulling the cap longitudinally in the proximal direction P. As the needle cap 110B and accompanying needle cap seal 305C move longitudinally in the proximal direction relative to the needle tip cover, the inwardly projecting barbs 305D on the needle cap seal 305C embed within the needle tip cover, causing the needle tip cover to be pulled off or otherwise released from the needle holder 314 when the needle cap 110 is removed. Once the needle tip cover is removed, the proximal end P of the auto-injector device 110 is pressed against the skin (injection site), causing the cartridge assembly 340 to move longitudinally in the proximal direction P until reaching a stop, such that the distal end of the needle 312 pierces the septum 344 on the cartridge 340.

Operation of a Semi-Disposable Auto-Injector Device 100

Once the needle cap 110 is removed from the assembled auto-injector device 100 (causing the needle assembly 310 to move longitudinally in the distal direction D until the injection needle 312 pierces the seal 332 and the septum 344 of the cartridge assembly 340), the needle assembly 310 is locked in its final position within cartridge holder 330 by engagement of the flexible hook-shaped member 414 extending from the needle holder 314 within a corresponding opening 640 in the cartridge holder. Removal of the needle cap 110 releases the needle shield 320 to allow movement longitudinally relative the front subassembly shell 300. Referring to FIGS. 11A and 11B and as will be explained in greater detail below, the needle shield 320 is biased in the proximal direction P by needle shield springs 1152 acting on the needle shield ring 1150 (FIG. 11H).

Referring to FIGS. 9 and 10, when the needle shield 320 is depressed (e.g. pressed against the skin or injection site of the patient), the needle shield 320 moves longitudinally in a distal direction D (Arrow E in FIG. 8). As the needle shield 320 moves longitudinally, the ramps 1020 on the needle shield 320 engage the corresponding ramps 1030 on the front subassembly shell 300, causing the flexible tabs 830 to flex or otherwise move outward to disengage the release latch 832 from the corresponding opening 640 in the distal end of the cartridge holder 330. Once disengaged, the cartridge holder 330 is able to move longitudinally in the proximal direction P (Arrow D in FIG. 8) to perform needle penetration and drug delivery.

FIG. 11C is an enlarged view of the trigger lock 1130 and release latch 1140 illustrated in circle 1112 of FIG. 11A. The plunger 1110 passes through an opening in the release latch 1140. The proximal end of the plunger 1110 preferably includes a shoulder 1111 (FIG. 11G). Referring to FIG. 11C, the release latch 1140 includes one or more flexible arms 1141 terminating in an enlarged head 1142 that releasably engages the shoulder 1111 to prevent the plunger 1110 from moving longitudinally in the proximal direction P (Arrow F in FIG. 11C) until the needle shield 320 is depressed fully or at least a minimum predetermined distance to activate the auto-injector device 100. Referring to FIG. 13, when the needle shield 320 is fully depressed, the trigger lock 1130 (FIG. 11J) is moved longitudinally in the distal direction D (Arrow G in FIG. 11C), which causes the one or more flexible arms 1141 on the release latch 1140 to flex or bend radially outward to release the plunger 1110 and allow it to move longitudinally in the proximal direction P (Arrow F in FIG. 11C) to begin needle penetration.

Figure 14:
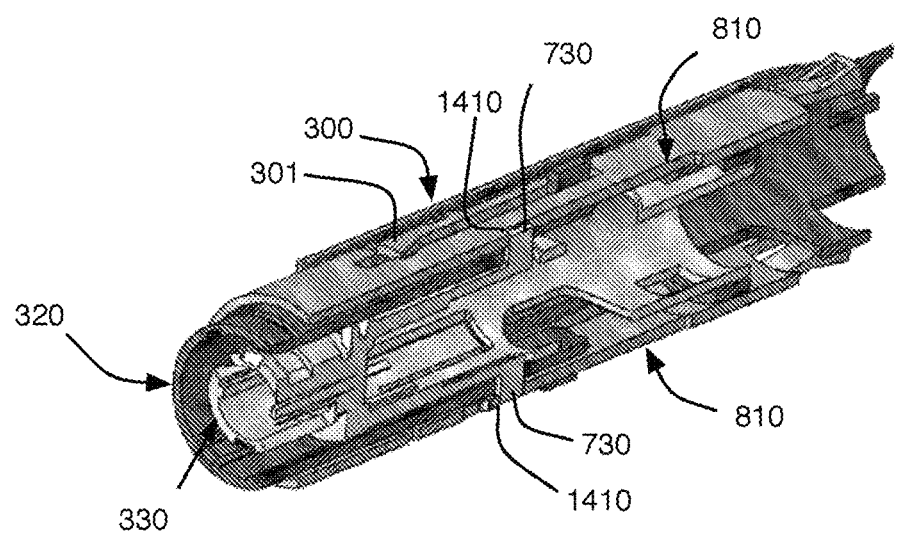
FIG. 14 is a cross section of a proximal portion of front subassembly of the auto-injector device during needle penetration.

Referring to FIGS. 11A, 13 and 14, once the cartridge holder 330 is released from the disposable housing front subassembly shell 300 and the plunger 1110 moves longitudinally in the proximal direction P (Arrow F in FIGS. 11C and 11D) under the force of plunger spring 1122, the cartridge holder 330 is pushed longitudinally by the plunger 1110 acting on the stopper 348 in the proximal direction P (Arrow F in FIGS. 11C and 11D) until the one or more splines 730 on the cartridge holder 330 bottom out against the proximal end 1410 of the axial groove or track 810 in the front subassembly shell 300 to prevent further movement of the cartridge holder 330 in the proximal direction P.

Figure 15:
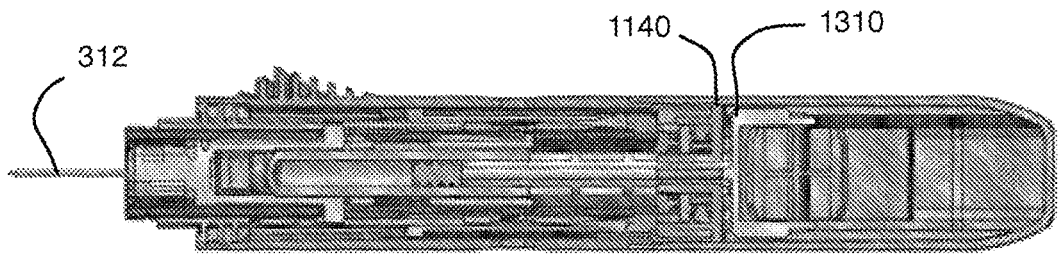
FIG. 15 is a cross-section of the auto-injector device of FIG. 11 at the end of drug delivery.

Referring to FIGS. 13 and 15, the plunger 1110 will continue to move longitudinally in the proximal direction P, causing the stopper 348 to also move longitudinally in the same direction P within the cartridge body 342 to deliver medication M through injection needle 312. The plunger 1110 will continue to move longitudinally in the proximal direction P until the distal flange 1310 of the plunger 1110 engages the distal end of the release latch 1140, which represents the end of the predefined dosage of medication M to be delivered to the patient.

Figure 16:
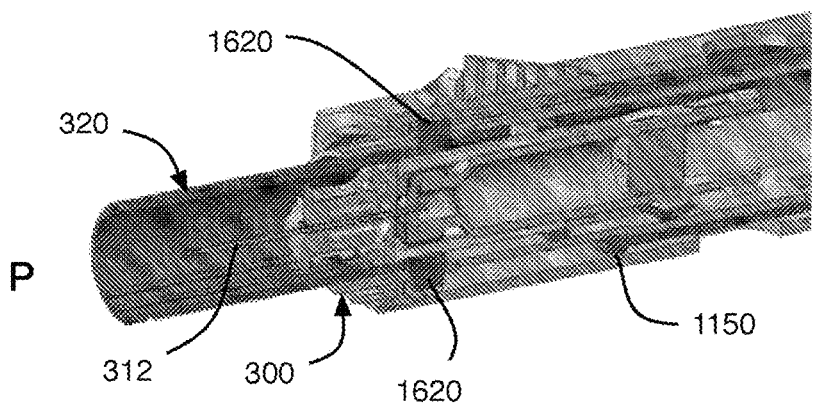
FIG. 16 is a cross-section of a proximal portion of the auto-injector device of FIG. 11 at needle cover lockout after the device is moved away from the injection site following drug delivery.
Figure 17:
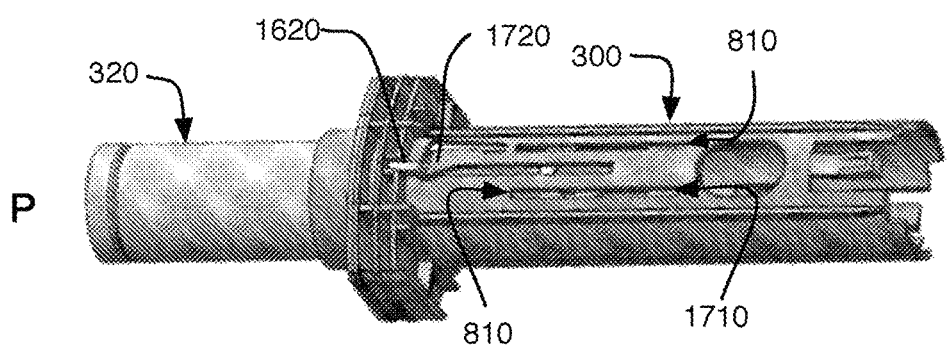
FIG. 17 illustrates the needle shield and disposable housing of FIG. 16.
Figure 18:
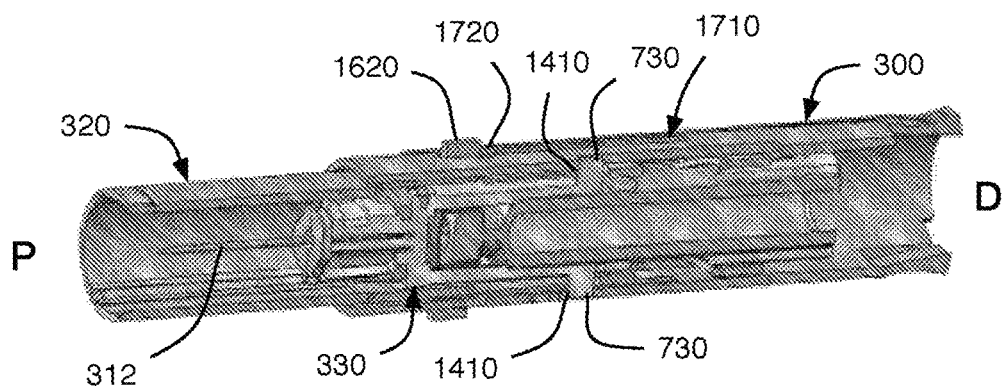
FIG. 18 is a cross section of the disposable body assembly with the needle shield locked in the fully extended position following drug delivery.

Referring to FIGS. 16-18, the needle shield 320 preferably includes one or more outwardly extending splines 1620 that are constrained by and move longitudinally within a corresponding channel or track 1710 formed on the front subassembly shell 300 when the needle shield moves longitudinally relative to the disposable housing. Once the medication M is delivered and the auto-injector device 100 is moved away from the patient's skin (injection site), the needle shield spring ring 1150 (under the force of the needle shield springs 1152) pushes the needle shield 320 longitudinally in the proximal direction P until one or more outwardly projecting splines 1620 on the needle shield 320 pass a corresponding flexible retaining tab 1720 extending into the axial channel 1710 near the proximal end of the disposable housing 300 to lock the needle shield in the extended or forward-most position. In the extended position, the needle shield 320 surrounds the injection needle 312 so that the injection needle 312 is not exposed after use of the auto-injector device 100.

Referring to FIG. 18, once removed from the auto-injector device 100, the entire disposable body assembly 130 is locked. The needle shield 320 is prevented from moving longitudinally in either direction by the retaining tabs 1720 formed on the front subassembly shell 300, which extend into the channel 1710 to constrain corresponding splines 1620 on the needle shield. Similarly, the cartridge holder 330 is prevented from moving longitudinally in the distal direction D by the needle shield 320 and from moving longitudinally in the proximal direction P by the front subassembly shell 300, as the one or more splines 730 on the cartridge holder 330 are locked between the needle shield and the front subassembly shell.

Figure 19:
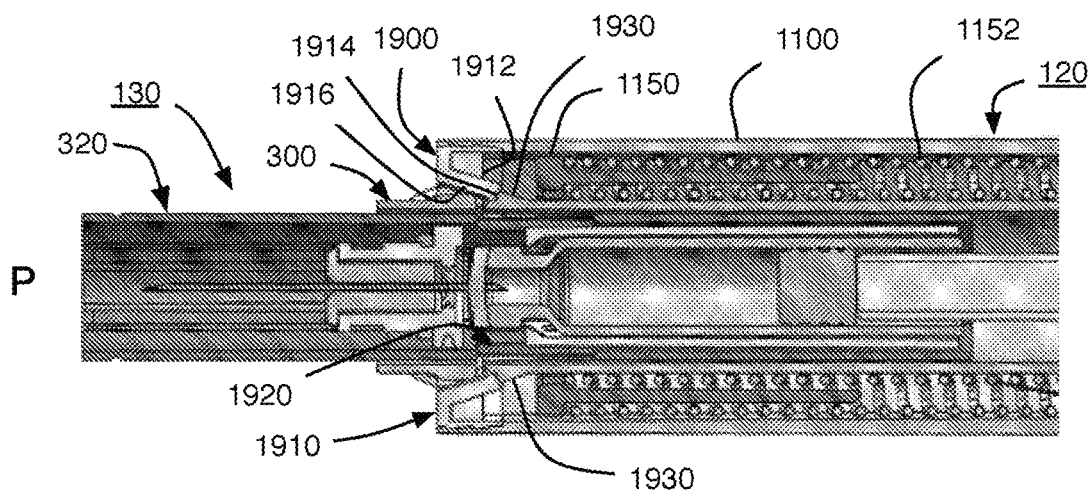
FIG. 19 is a cross section of a proximal portion of the auto-injector device of FIG. 11 after the needle shield is locked in the fully extended position.
Figure 20:
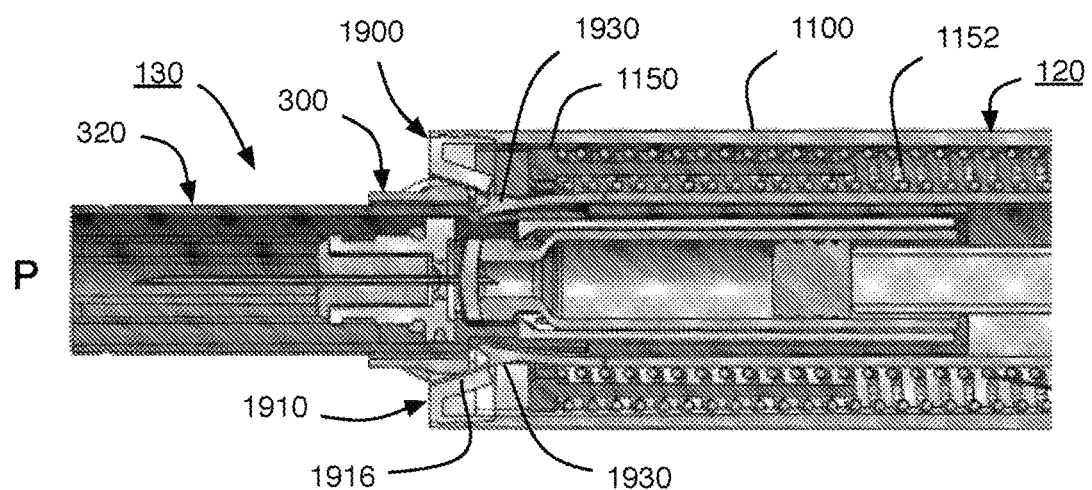
FIG. 20 is a cross section of the proximal portion of a semi-disposable auto-injector as the disposable body assembly is initially released from the reusable body assembly.
Figure 21:
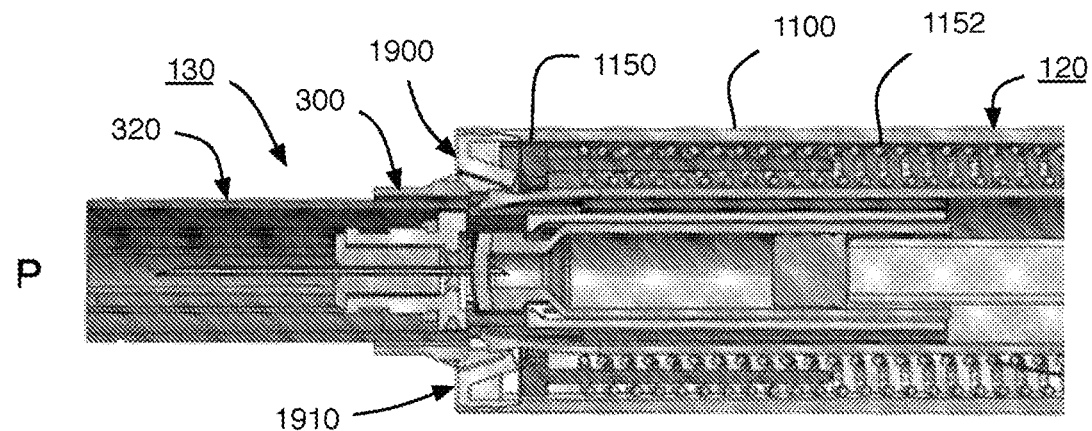
FIG. 21 is a cross section of the proximal portion of the semi-disposable auto-injector device of FIG. 20 as the disposable body assembly is fully released from the reusable body assembly.

Referring to FIGS. 19-21, once the needle shield 320 is locked, the needle shield spring ring 1150 (under the force of the needle shield ring spring 1152) continues to push the needle shield 320 longitudinally in the proximal direction P until it abuts against a retaining tab or flange 1910 on the reusable body front cap 1900 affixed to the proximal end 1101 of the reusable housing 1100. The retaining tab 1910 includes a generally flat portion 1912, a tapered disassembly portion 1914, and a tapered assembly portion 1916.

When the needle shield 320 is fully extended, an opening 1920 formed in the needle shield 320 is aligned with flexible retaining tabs 1930 on the disposable housing 300. Since the entire disposable body assembly 130 is pushed forward in the proximal direction P by the needle shield spring ring 1150, engagement of the disposable housing retaining tabs 1930 with the tapered portion 1914 of the proximal retaining tab 1910 on the reusable housing 1100 causes the retaining tabs 1930 to bend or flex radially inward into the aligned opening 1920 formed in the needle shield 320. This allows the disposable body assembly 130 to separate slightly from the reusable body assembly 120. As illustrated in FIG. 21, the disposable body assembly 130 is released from the reusable body assembly 120 and can be discarded.

A new (unused) disposable body assembly 130 may be inserted into and releasably connected to the reusable body assembly 120. When inserting a new (unused) disposable body assembly 130 into the reusable body assembly 120, the opening 1920 in the needle shield 320 is not aligned with the retaining tabs 1930 on the disposable housing 130 and the needle shield prevents the retaining tabs 1930 from flexing inward.

During recharging of the semi-disposable auto-injector device 100, the flexible retaining tabs 1910 on the reusable housing 1100 bend or flex so that the disposable body assembly 130 and reusable body assembly 120 can be releasably connected. The retaining tabs 1910 on the reusable housing 1100 are preferably made more rigid than the disposable housing retaining tabs 1930 and include a high assembly angle and low disassembly angle so that the reusable housing retaining tabs 1910 do not easily flex radially outward when the auto-injector device 100 is assembled.

During assembly of the disposable body assembly 130, the stopper 348 on the cartridge body 342 pushes the plunger 1110 longitudinally in the distal direction D to the loaded position. Once the plunger 1110 is pushed past the stable loaded position, the trigger lock 1130 will freely move longitudinally in the proximal direction P under the force of the trigger spring 1131 and the enlarged head 1242 on the flexible arm 1240 of release latch 1140 releasably engages the shoulder 1210 on the plunger 1110 to releasably lock the plunger until the needle shield 320 is fully depressed to activate the auto-injector device 100.

Figure 22:
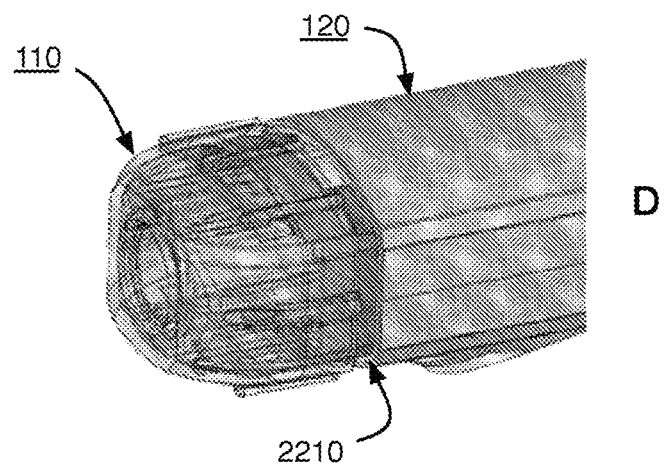
FIG. 22 is a perspective view of the proximal portion of the auto-injector device of FIG. 1 that includes a cap spacer.
Figure 23:
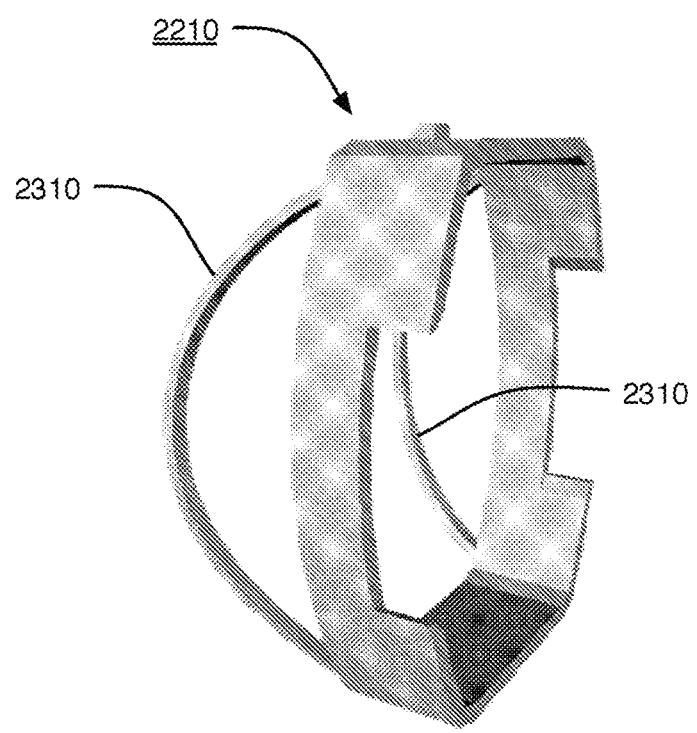
FIG. 23 is a perspective view of the cap spacer.

FIGS. 22 and 23 illustrate a cap spacer 2210, which functions to fill the empty space between the cap 110 and the reusable body assembly 120 of the auto-injector device 100 once the device is assembled. When assembling the new disposable body assembly 130, after disposing of the used one, the device 100 needs to be pushed past the point where the plunger 1110 will reset. To allow for an extra push space in the distal direction D when the disposable body assembly 130 is being assembled, the device 100 has a small space between the distal end of the cap 110 and the reusable body 120. The cap spacer 2210 preferably includes one or more spring or resilient members 2310 that allow the spacer to move into the cap 110 when the disposable body assembly 130 is being assembled and then spring out to fill out the empty space between the cap 110 and the reusable body 120.

Figure 24:
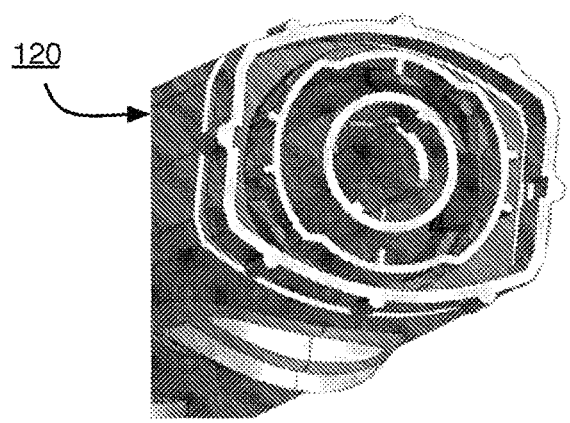
FIG. 24 is a front perspective view of the reusable body front cap mounted on the reusable body.
Figure 25:
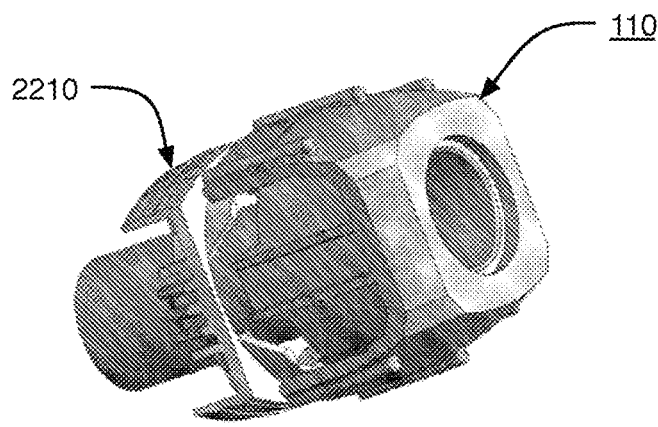
FIG. 25 is a perspective view of the needle cap and reusable body front cap.
Figure 26:
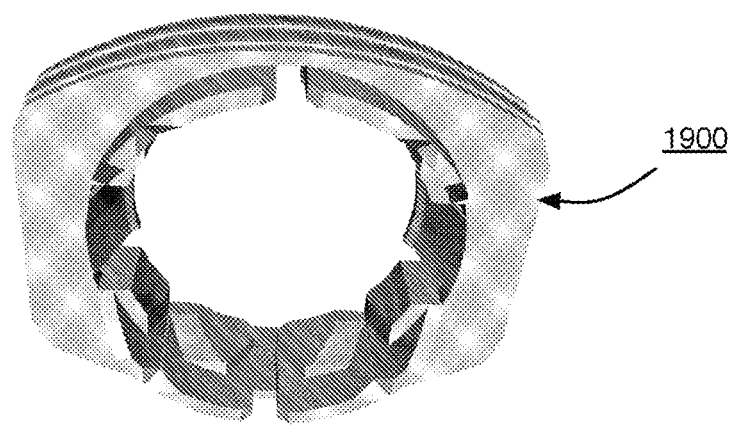
FIG. 26 is a perspective view of the reusable body front cap.

Referring to FIGS. 24-25, the needle cap 110 includes a feature that engages with a raised wall with a ramp at the beginning on the reusable body front cap 1900. This prevents the cap 110 from being pushed against the reusable body when the cap is turned. If this feature was not in place and the needle cap 110 is pushed when turned, the septum 344 of the cartridge assembly 340 may hit the plunger 1110, which will result in a mis-dose when the device is used.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. An auto-injector for hypodermic delivery of medication, comprising:
 a first subassembly releasably coupled to a second subassembly;
  wherein the first subassembly includes
   a cartridge holder configured to receive a medication cartridge,
   a hollow injection needle having a longitudinal cavity through which medication can pass from the medication cartridge, and
   a needle shield moveable relative to the cartridge holder between an extended position enclosing the needle and a retracted position in which at least a proximal end of the needle is not enclosed by the needle shield; and wherein the second subassembly includes
a housing, and
a moveable plunger rod positioned within the housing,
wherein movement of the needle shield in a proximal direction from the retracted position to the extended position will automatically disconnect the first subassembly from the second subassembly.

2. The auto-injector of claim 1, wherein the first subassembly further comprises:
a needle holder for retaining the needle, wherein the needle holder is moveable between a first position and a second position, wherein, in the first position, the needle cavity is not in fluid communication with an interior of the medication cartridge, and in the second position, the needle cavity is in fluid communication with the interior of the medication cartridge, and
a cap, releasably attached to the first subassembly, such that during removal of the cap from the first subassembly, the needle moves from the first position to the second position so as to cause a distal end of the needle to pierce a septum of the cartridge.

3. The auto-injector of claim 2, wherein the cap includes a cam follower for engaging a cam on the needle holder such that rotation of the cap in at least one direction causes distal movement of the needle holder and needle toward the second position.

4. The auto-injector of claim 2, wherein the cap includes a spring, such that rotation of the cap in at least one direction releases of the spring, which engages and causes distal movement of the needle holder and needle toward the second position.

5. The auto-injector of claim 1, wherein the first subassembly further comprises:
a shell, at least partially encompassing the cartridge holder and the needle shield, and
a cap, releasably attached to the first subassembly, wherein the cap releasably locks the shell and needle shield such that, when in place on the first subassembly, the cap prevents the needle shield and shell from moving relative to each other and, when the cap is removed from the first subassembly, the needle shield can move relative to the shell.

6. The auto-injector of claim 1, wherein distal movement of the needle shield from the extended position to the retracted position causes propulsion of medication through the needle.

7. The auto-injector of claim 6, wherein the second subassembly further comprises:
a plunger release latch positioned within the housing to releasably retain the plunger rod in a locked position,
wherein the cartridge holder is moveable between a first position and a second position proximal from the first position, such that, in the first position, the cartridge holder is prevented from moving in a proximal direction, and
wherein distal movement of the needle shield to the retracted position releases the cartridge holder from the first position and releases the latch to allow the plunger rod to move in the proximal direction and urge the cartridge holder from the first position to the second position.

8. The auto-injector of claim 7, wherein the first subassembly further comprises:

a shell, at least partially encompassing the cartridge holder and the needle shield,
wherein releasable engagement of the shell with the cartridge holder prevents the cartridge holder from moving in the proximal direction when the cartridge holder is in the first position.

9. The auto-injector of claim 8, wherein the cartridge holder includes at least one flexible tab that releasably engages the shell to prevent the cartridge holder from moving in the proximal direction when the cartridge holder is in the first position.

10. The auto-injector of claim 8, wherein the shell includes at least one flexible tab that releasably engages the cartridge holder to prevent the cartridge holder from moving in the proximal direction when the cartridge holder is in the first position.

11. The auto-injector of claim 6, wherein, after the plunger rod is released and causes the cartridge holder to move proximally from the first position to the second position, the plunger rod continues to move in the proximal direction to engage and move a stopper within the medicine cartridge.

12. The auto-injector of claim 1, wherein the first subassembly further comprises:
a shell, at least partially encompassing the cartridge holder and the needle shield,
wherein the shell includes at least one outwardly projecting flexible tab for engaging a corresponding at least one inwardly projecting retaining tab on the housing to releasably couple the first subassembly to the second subassembly.

13. The auto-injector of claim 12, wherein the second subassembly further comprises:
a movable ring that is biased in the proximal direction such that, when the needle shield moves proximally from the retracted position to the extended position, the ring engages the at least one flexible tab on the shell to disengage the at least one flexible tab from the corresponding at least one retaining tab on the housing.

14. The auto-injector of claim 13, wherein the needle shield includes an opening aligned with the flexible tab when the needle shield has moved from the retracted position to the extended position to allow the ring to cause the flexible tab on the shell to flex into the opening and disengage the flexible tab from the corresponding retaining tab on the housing.

15. The auto-injector of claim 1, wherein the needle shield includes at least one spline that travels within and is constrained by a corresponding groove formed in the shell, such that, when the needle shield moves from the retracted position to the extended position, the spline engages a tab on the shell extending into the groove to lock the needle shield in the extended position.

16. The auto-injector of claim 1, wherein the first subassembly is a single-use subassembly.

17. The auto-injector of claim 1, wherein the second subassembly is a multiple-use subassembly.

18. An auto-injector for hypodermic delivery of medication comprising:
a housing;
a medication cartridge positioned within the housing, the cartridge including a pierceable septum;
a cartridge holder positioned within the housing and configured to receive the medication cartridge, the cartridge holder being moveable between a first position and a second position proximal from the first position, wherein, in the first position, the cartridge holder is prevented from moving in a proximal direction;

a hollow injection needle having a longitudinal cavity therethrough and positioned within the housing, the needle being moveable between a first position and a second position, wherein, in the first position, the needle cavity is not in fluid communication with an interior of the cartridge, and in the second position, the needle cavity is in fluid communication with the interior of the cartridge;

a cap, releasably attached to the housing, such that during removal of the cap from the housing, the needle moves from the first position to the second position so as to cause a distal end of the needle to pierce the septum of the cartridge;

a moveable plunger rod positioned within the housing and biased to move in the proximal direction;

a plunger release latch positioned within the housing to releasably retain the plunger rod in a locked position; and a moveable needle shield that moves from an extended position in which the needle shield is extended proximally beyond the needle to a retracted position where at least an end of the needle is exposed during injection; and wherein retraction of the needle shield to the retracted position causes propulsion of medication through the needle and wherein distal movement of the needle shield to the retracted position releases the cartridge holder from the first position and releases the latch to allow the plunger rod to move in the proximal direction and urge the cartridge holder from the first position to the second position.

19. The auto-injector of claim 18, further comprising:
a shell at least partially encompassing the cartridge holder and the needle shield; and
wherein releasable engagement of the shell with the cartridge holder prevents the cartridge holder from moving in the proximal direction when the cartridge holder is in the first position.

20. The auto-injector of claim 18, wherein, after the plunger rod is released and causes the cartridge holder to move to the second position, the plunger rod continues to move in the proximal direction to engage and move a stopper within the medicine cartridge.

21. The auto-injector of claim 18, further comprising:
a first subassembly releasably coupled to a second subassembly; and
wherein the first subassembly comprises the needle, the cartridge holder, the needle shield, and a shell, and the second subassembly comprises the housing, the moveable plunger rod, and the release latch.

22. The auto-injector of claim 21, wherein movement of the needle shield from the retracted position to the extended position will automatically release the first subassembly from the second subassembly.

23. The auto-injector of claim 21, wherein the first subassembly is a single-use subassembly.

24. The auto-injector of claim 21, wherein the second subassembly is a multiple-use subassembly.

25. An auto-injector for hypodermic delivery of medication, comprising:
a housing;
a cartridge holder positioned within the housing and configured to receive a medication cartridge, the cartridge holder being moveable between a first position and a second position proximal from the first position, wherein, in the first position, the cartridge holder is prevented from moving in a proximal direction;

a moveable plunger rod positioned within the housing and biased to move in the proximal direction;

a plunger release latch positioned within the housing to releasably retain the plunger rod in a locked position;

a hollow injection needle having a longitudinal cavity through which medication can pass from the medication cartridge; and a needle shield movable relative to the cartridge holder between an extended position enclosing the needle and a retracted position in which at least an end of the needle is not enclosed by the needle shield;

a. wherein distal movement of the needle shield both releases the cartridge holder from the first position and releases the latch to cause the plunger rod to move in the proximal direction and urge the cartridge holder from the first position to the second position.

26. The auto-injector of claim 25, further comprising:
a shell, at least partially encompassing the cartridge holder and the needle shield; and
wherein releasable engagement of the shell with the cartridge holder prevents the cartridge holder from moving in the proximal direction when the cartridge holder is in the first position.

27. The auto-injector of claim 26, further comprising:
at least one flexible tab on the cartridge holder that releasably engages the shell to prevent the cartridge holder from moving in the proximal direction when the cartridge holder is in the first position.

28. The auto-injector of claim 26, further comprising:
at least one flexible tab on the shell that releasably engages the cartridge holder to prevent the cartridge holder from moving in the proximal direction when the cartridge holder is in the first position.

29. The auto-injector of claim 25, wherein, after the plunger rod is released and causes the cartridge holder to move to the second position, the plunger rod continues to move in the proximal direction to engage and move a stopper within the medicine cartridge.

30. The auto-injector of claim 25, further comprising:
a removable cap, releasably attached to the housing, such that during removal of the cap from the housing, the needle moves from a first position where the needle cavity is not in fluid communication with an interior of the cartridge to a second position where the needle cavity is in fluid communication with the interior of the cartridge.

31. The auto-injector of claim 30, further comprising:
a movable needle holder for retaining the needle; and
wherein the cap includes a cam follower for engaging a cam on the needle holder such that rotation of the cap in at least one direction causes distal movement of the needle holder and needle toward the second position.

32. The auto-injector of claim 30, further comprising:
a movable needle holder for retaining the needle; and
wherein the cap includes a spring such that rotation of the cap in at least one direction releases of the spring, which engages and causes distal movement of the needle holder from the first position toward the second position.

33. The auto-injector of claim 25, further comprising:
a shell, at least partially encompassing the cartridge holder and the needle shield; and a removable cap, releasably attached to the housing, the cap releasably locking the shell and needle shield such that, when attached to the housing, the cap prevents the needle shield and shell from moving relative to each other and, when removed, the cap allows relative movement between the shell and needle shield.

34. The auto-injector of claim 25, further comprising:
a first subassembly releasably coupled to a second subassembly; and
wherein the first subassembly includes the needle, the cartridge holder, the needle shield, and a shell, and the second subassembly includes the housing, the moveable plunger rod, and the release latch.

35. The auto-injector of claim 34, wherein movement of the needle shield from the retracted position to the extended position will automatically release the first subassembly from the second subassembly.

36. The auto-injector of claim 35, wherein the first subassembly is a single-use subassembly.

37. The auto-injector of claim 35, wherein the second subassembly is a multiple-use subassembly.

38. The auto-injector of claim 35, wherein the shell includes at least one outwardly projecting flexible tab for engaging a corresponding at least one inwardly projecting retaining tab on the housing to releasably couple the first subassembly to the second subassembly.

39. The auto-injector of claim 38, wherein the second subassembly further comprises:
a ring that is biased in the proximal direction such that, when the needle shield moves from the retracted position to the extended position, the ring engages the at least one flexible tab on the shell to disengage the at least one flexible tab from the at least one retaining tab on the housing.

40. The auto-injector of claim 39, wherein the needle shield includes an opening aligned with the flexible tab when the needle shield has moved from the retracted position to the extended position to allow the ring to cause the flexible tab on the shell to flex into the opening and disengage the flexible tab from the corresponding retaining tab on the housing.

41. The auto-injector of claim 30, wherein the needle shield includes a spline that travels within and is constrained by a groove formed in the shell, such that, when the needle shield moves from the retracted position to the extended position, the spline engages a tab on the shell extending into the groove to lock the needle shield in the extended position.

42. A subassembly for an auto-injector, comprising:
a cartridge holder, configured to receive a medication cartridge;
a hollow injection needle having a longitudinal cavity therethrough through which medication can pass from the medication cartridge;
a needle shield movable relative to the cartridge holder between an extended position enclosing the needle and a retracted position in which at least an end of the needle is not enclosed by the needle shield;
a shell, at least partially encompassing the cartridge holder and the needle shield; and
a removable cap which releasably locks the shell and needle shield such that, when in place, the cap prevents the needle shield and shell from moving relative to each other and, when removed, allows relative movement between the shell and needle shield;
wherein the shell is configured to releasably connect to a second subassembly so as to form the auto-injector.

43. The auto-injector subassembly of claim 42, further comprising:
a needle holder for retaining the needle, wherein the needle holder is moveable between a first position and a second position, wherein, in the first position, the needle cavity is not in fluid communication with an interior of the medication cartridge, and in the second position, the needle cavity is in fluid communication with the interior of the medication cartridge.

44. The auto-injector subassembly of claim 43, wherein removal of the cap moves the needle holder from the first position to the second position such that needle cavity is in fluid communication with the interior of the medication cartridge.

45. The auto-injector subassembly of claim 44, wherein the cap includes a cam follower for engaging a cam on the needle holder such that rotation of the cap in at least one direction causes distal movement of the needle holder and needle toward the second position.

46. The auto-injector subassembly of claim 44, wherein the cap includes a spring, such that rotation of the cap in at least one direction releases of the spring, which engages and causes distal movement of the needle holder and needle toward the second position.

47. The auto-injector subassembly of claim 42, wherein the cartridge holder is moveable between a first position and a second position proximal from the first position, wherein, in the first position, the cartridge holder is prevented from moving in a proximal direction.

48. The auto-injector subassembly of claim 47, wherein a releasable locking member affixed to one of the cartridge holder or shell engages the other of the cartridge holder or shell to prevent relative motion between the cartridge holder and shell in at least one direction when the locking member is engaged.

49. The auto-injector subassembly of claim 48, wherein movement of the needle shield from the extended position to the retracted position disengages the releasable locking member to permit the cartridge holder to move in the proximal direction from the first position to the second position.

50. The auto-injection subassembly of claim 42, wherein the subassembly is a single-use subassembly.

* * * * *